(12) United States Patent
Haaland et al.

(10) Patent No.: US 6,842,702 B2
(45) Date of Patent: Jan. 11, 2005

(54) AUGMENTED CLASSICAL LEAST SQUARES MULTIVARIATE SPECTRAL ANALYSIS

(75) Inventors: David M. Haaland, Albuquerque, NM (US); David K. Melgaard, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/661,968

(22) Filed: Sep. 11, 2003

(65) Prior Publication Data

US 2004/0064259 A1 Apr. 1, 2004

Related U.S. Application Data

(62) Division of application No. 10/209,841, filed on Jul. 31, 2002, now Pat. No. 6,687,620.
(60) Provisional application No. 60/311,755, filed on Aug. 9, 2001, and provisional application No. 60/309,619, filed on Aug. 1, 2001.

(51) Int. Cl.[7] .......................... G06F 19/00; G01N 33/48
(52) U.S. Cl. ........................... 702/18; 250/573; 702/22; 702/27; 702/28
(58) Field of Search ............................... 702/22–26, 27, 702/28, 30, 181, 189–190, 196–199; 250/339.08, 339.09, 339.12, 559.1, 573

(56) References Cited

U.S. PATENT DOCUMENTS

| | | | | |
|---|---|---|---|---|
| 5,121,337 A | * | 6/1992 | Brown | ......................... 702/28 |
| 6,341,257 B1 | * | 1/2002 | Haaland | ........................ 702/27 |
| 6,415,233 B1 | * | 7/2002 | Haaland | ........................ 702/22 |
| 6,528,809 B1 | * | 3/2003 | Thomas et al. | ............. 250/573 |

* cited by examiner

*Primary Examiner*—John Barlow
*Assistant Examiner*—John Le
(74) *Attorney, Agent, or Firm*—Kevin W. Bieg

(57) ABSTRACT

A method of multivariate spectral analysis, termed augmented classical least squares (ACLS), provides an improved CLS calibration model when unmodeled sources of spectral variation are contained in a calibration sample set. The ACLS methods use information derived from component or spectral residuals during the CLS calibration to provide an improved calibration-augmented CLS model. The ACLS methods are based on CLS so that they retain the qualitative benefits of CLS, yet they have the flexibility of PLS and other hybrid techniques in that they can define a prediction model even with unmodeled sources of spectral variation that are not explicitly included in the calibration model. The unmodeled sources of spectral variation may be unknown constituents, constituents with unknown concentrations, nonlinear responses, non-uniform and correlated errors, or other sources of spectral variation that are present in the calibration sample spectra. Also, since the various ACLS methods are based on CLS, they can incorporate the new prediction-augmented CLS (PACLS) method of updating the prediction model for new sources of spectral variation contained in the prediction sample set without having to return to the calibration process. The ACLS methods can also be applied to alternating least squares models. The ACLS methods can be applied to all types of multivariate data.

48 Claims, 25 Drawing Sheets

$$\hat{\tilde{K}} = (\tilde{C}^T \tilde{C})^{-1} \tilde{C}^T$$

$$e = \hat{c} - c$$

$$\hat{\tilde{K}} = (\tilde{C}^T \tilde{C})^{-1} \tilde{C}^T$$

$$= \begin{bmatrix} c_1 & c_1 & \ldots & c_{1n} \\ 1 & 2 & \ldots & c \\ c_2 & c_2 & \ldots & c \end{bmatrix}^{-1} \begin{bmatrix} c_1 & c_1 & \ldots & c_{1n} \\ 1 & 2 & \ldots & c \\ c_2 & c_2 & \ldots & c \end{bmatrix} \begin{bmatrix} c_1 e & c_1 e & \ldots & c e \\ c_2 & c_2 & \ldots & c \end{bmatrix}$$

$$e = \hat{c} - c$$

Fig. 1

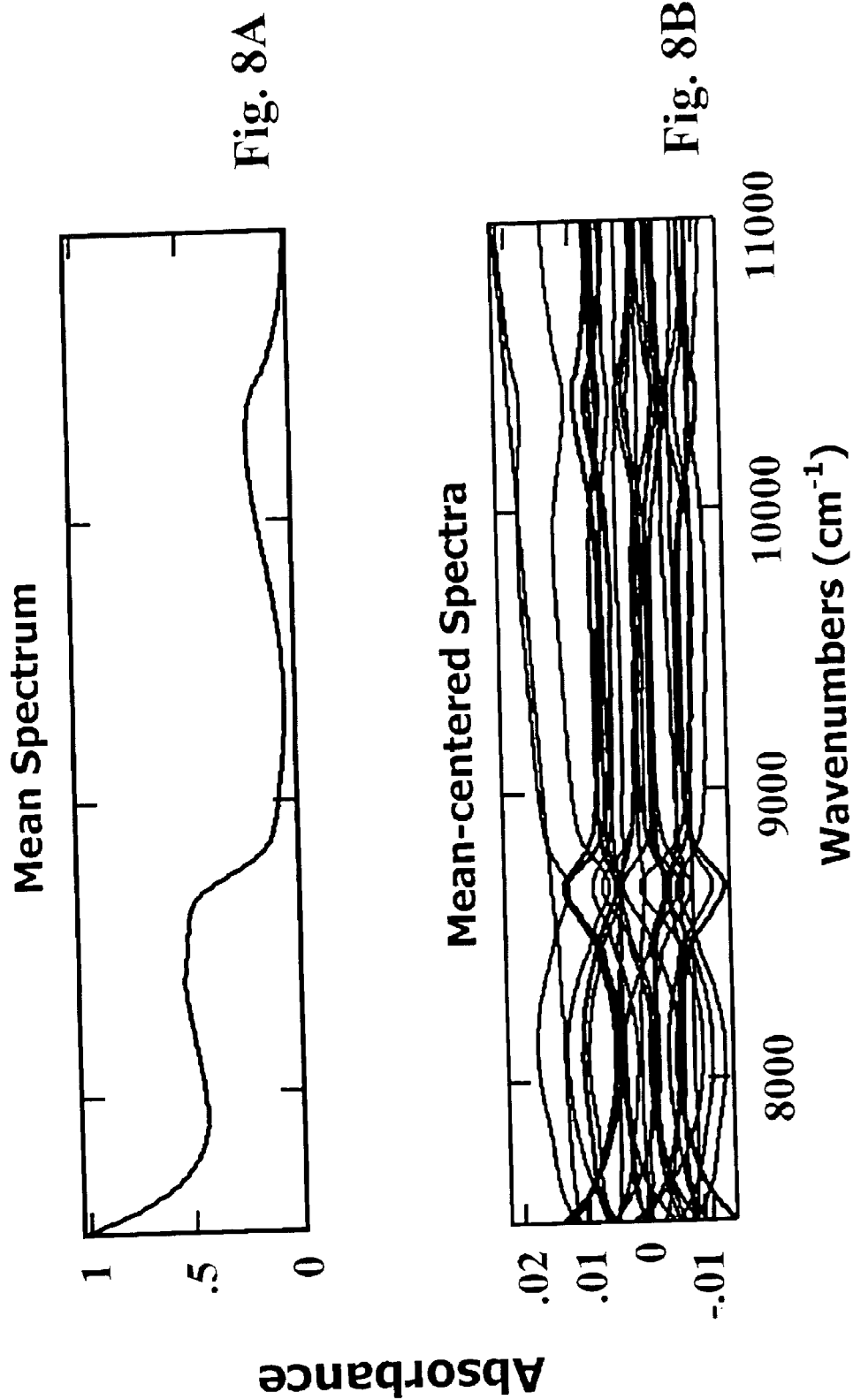

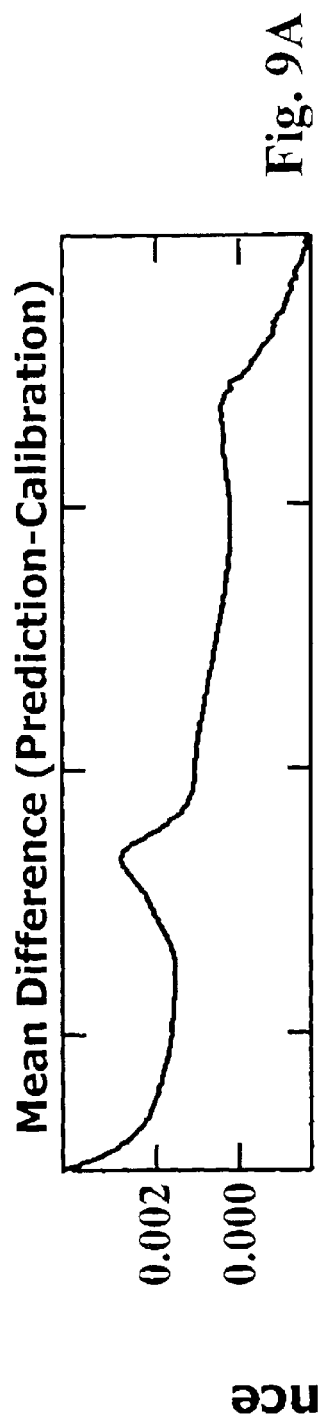
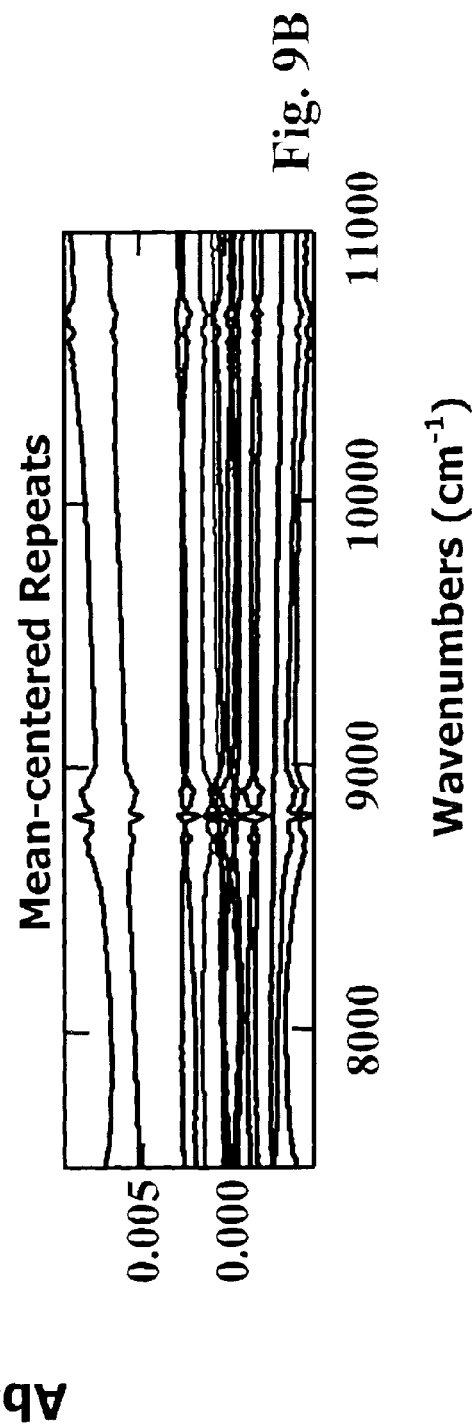
Fig. 9A
Fig. 9B

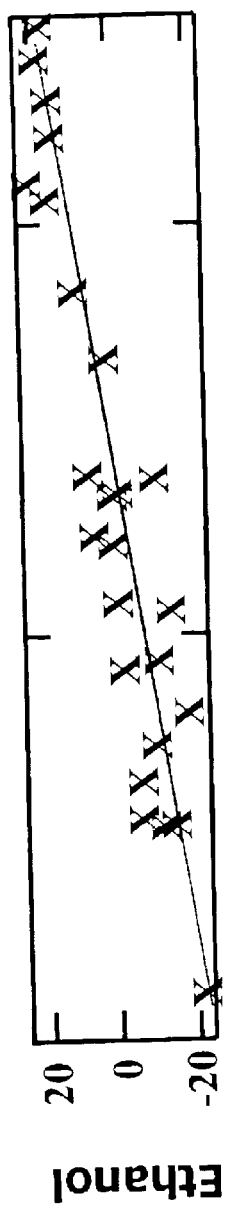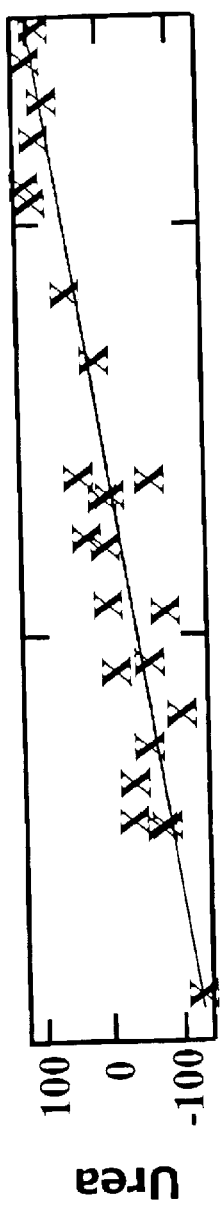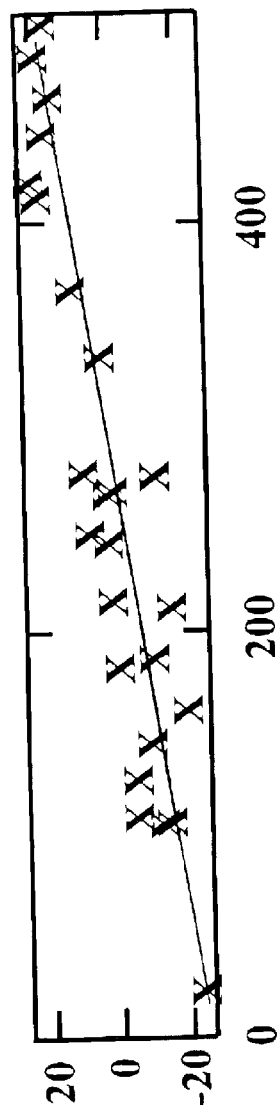
Fig. 10A
Fig. 10B
Fig. 10C

AUGMENTED CLASSICAL LEAST SQUARES MULTIVARIATE SPECTRAL ANALYSIS

RELATED INVENTIONS

This application is a divisional of application Ser. No. 10/209,841, filed Jul. 31, 2002 now U.S. Pat. No. 6,687,620, application Ser. No. 10/209,841 claims the benefit of Provisional Application No. 60/309,619, filed on Aug. 1, 2001, and Provisional Application No. 60/311,755, filed on Aug. 9, 2001.

GOVERNMENT RIGHTS

The Government has rights to this invention pursuant to Contract No. DE-AC04-94AL85000 awarded by the U.S. Department of Energy.

FIELD OF THE INVENTION

The present invention relates generally to the field of multivariate spectral analysis and, more particularly, to a method for augmenting a classical least squares calibration model to provide improved predictions of component values in unknown samples having unmodeled sources of spectral variation.

BACKGROUND OF THE INVENTION

Over the past 20 years, quantitative multivariate spectral analysis has primarily shifted from the explicit classical least squares (CLS) method to the implicit principal component regression (PCR) and partial least squares (PLS) methods. The principle motivation for this shift is that CLS is based on an explicit linear additive model, e.g., the Beer-Lambert law. As such, CLS has the significant limitation that it requires the concentrations of all spectrally active components be known and included in the calibration model before an adequate prediction model can be developed. On the other hand, the PCR and PLS methods can achieve excellent predictions for multivariate spectral data sets where all of the spectrally active components have not been determined. Consequently, CLS has been relegated to solving a small set of well-defined linear problems with known spectrally active components that adhere to the Beer-Lambert law, e.g., infrared spectra of gas-phase samples.

Nevertheless, PCR and PLS do not have the qualitative capabilities of CLS since they do not generate explicit estimated pure-component spectra that can be readily interpreted. Also, they are not well suited to the advantages of a newly developed prediction-augmented CLS (PACLS) technique as set forth in U.S. Pat. No. 6,415,233, which is incorporated by reference herein. The PACLS algorithm provides a basis for rapidly updating a CLS model during prediction of component values of the target unknown sample. PACLS adds spectral shapes (i.e., spectral intensity information) to the CLS estimate of the pure-component spectra during prediction to account for spectrally active components or other spectral effects present in the prediction samples that were not modeled during calibration. PACLS allows CLS models to be updated for the presence of spectrometer drift, changes in spectrometer parts or changes in whole spectrometers, unmodeled chemical or non-chemical spectral components, as well as updating for more generalized changes such as changes in starting materials, the presence of nonlinearities, chromatic aberrations, or stray light, etc.

However, the PACLS algorithm is limited by the fact that accurate predictions require all interfering spectral components (including chemical and non-chemical sources of spectral variation) be explicitly included during calibration or prediction. If one or more spectral interferences were left out of the calibration, then their spectral influence would have to be explicitly added during prediction to correct for their absence in the calibration model.

These limitations of the CLS model can be reduced and even eliminated by the development of a new generalized family of algorithms, hereinafter referred to as augmented classical least squares (ACLS). The ACLS model uses information derived from component values and spectral residuals during the CLS calibration to provide an improved calibration-augmented CLS model. When the new ACLS methods are combined with the PACLS prediction algorithm, a powerful set of new multivariate capabilities is realized such that analyses can be performed with incomplete knowledge of interferences in the calibration and the prediction data.

The present invention further provides a generalization of ACLS methods for analyzing multivariate spectral data. Specific embodiments of the generalized ACLS methods are: spectral-residual augmented classical least squares (SRACLS), scores augmented classical least squares (SACLS), and concentration-residual augmented classical least squares (CRACLS) methods which all allow one to overcome the above deficiencies. The SRACLS, SACLS, and CRACLS methods are based on CLS so that they retain the qualitative benefits of CLS, yet they have the flexibility of PLS and other hybrid techniques in that they can define a prediction model even with unmodeled sources of spectral variation that are not explicitly included in the calibration model. The unmodeled sources of spectral variation may be unknown constituents, constituents with unknown concentrations, nonlinear responses, non-uniform and correlated errors, or other sources of spectral variation (e.g., temperature, spectrometer drift, etc.) that are present in the calibration sample spectra.

Augmentation can also be applied to constrained alternating classical least squares methods (alternating between CLS calibration and CLS prediction) that are used when the reference variables, such as the pure-component spectra or component concentrations, are inadequately known for standard CLS method. The ACLS methods of the present invention can improve the component identification with such inadequately known data sets.

Combining the present invention with the PACLS technique results in prediction models that are generally comparable or better in prediction ability to the standard PLS models. Also, since the various ACLS methods are based on CLS and unlike PLS, they can incorporate the PACLS feature of updating the prediction model for new sources of spectral variation without the need for time-consuming recalibration. These updated prediction models only require spectral information while PLS requires spectral and concentration information during recalibration. The present invention is not restricted to using continuous spectral information, but can also use any set of discontinuous spectral intensities that are selected in the calibration for the least squares analysis. Finally, the present invention generates better qualitative information about the analytes by generating better estimates of their pure-component spectra.

SUMMARY OF THE INVENTION

A method of multivariate spectral analysis is provided that is able to generate accurate and precise prediction models from multivariate spectral data which includes unmodeled spectrally active components present in the calibration model. The method provides the improved qualitative information of CLS methods as well as the quantitative prediction ability of the implicit multivariate calibration methods by augmenting the calibration model with a measure of the residual resulting from unmodeled components.

The present method of multivariate spectral analysis is most useful when an underlying calibration model includes unmodeled sources of spectral variation. In particular, reference variables (e.g., sample spectra and component values) are obtained for a set of calibration samples. An estimate is obtained for at least one reference variable for the set of calibration samples. Thereafter, a residual is obtained between the at least one reference variable and its corresponding estimated variable. A measure of the residual between the estimated and reference variable is used to augment its corresponding reference variable. Using the augmented reference variable, a value of at least one component in a set of unknown samples is predicted. Augmentation can be repeated until all sources of spectral variation are accounted for in the calibration samples. The iterative process allows the development of a CLS-type calibration model comparable in its quantitative prediction ability to implicit multivariate calibration methods, even when unmodeled spectrally active components are present in the calibration sample spectra.

BRIEF DESCRIPTION OF THE DRAWINGS

FIG. 1 depicts pictorially Eq. (16).

FIG. 8A depicts the mean spectrum and 8B depicts the mean-centered spectra of the calibration spectra.

FIG. 9A depicts the difference between average repeat spectra for the calibration and prediction data sets and 9B depicts the mean-centered average repeat spectra from the prediction data set.

FIGS. 10A, 10B and 10C depict the ethanol, urea and water concentration residuals, respectively, vs. the reference glucose concentration from the CLS model applied to the simulated data when leaving out glucose concentrations.

FIG. 14 shows examples of systematic artifacts in the spectral image scores

DETAILED DESCRIPTION OF THE INVENTION

Figure 2:
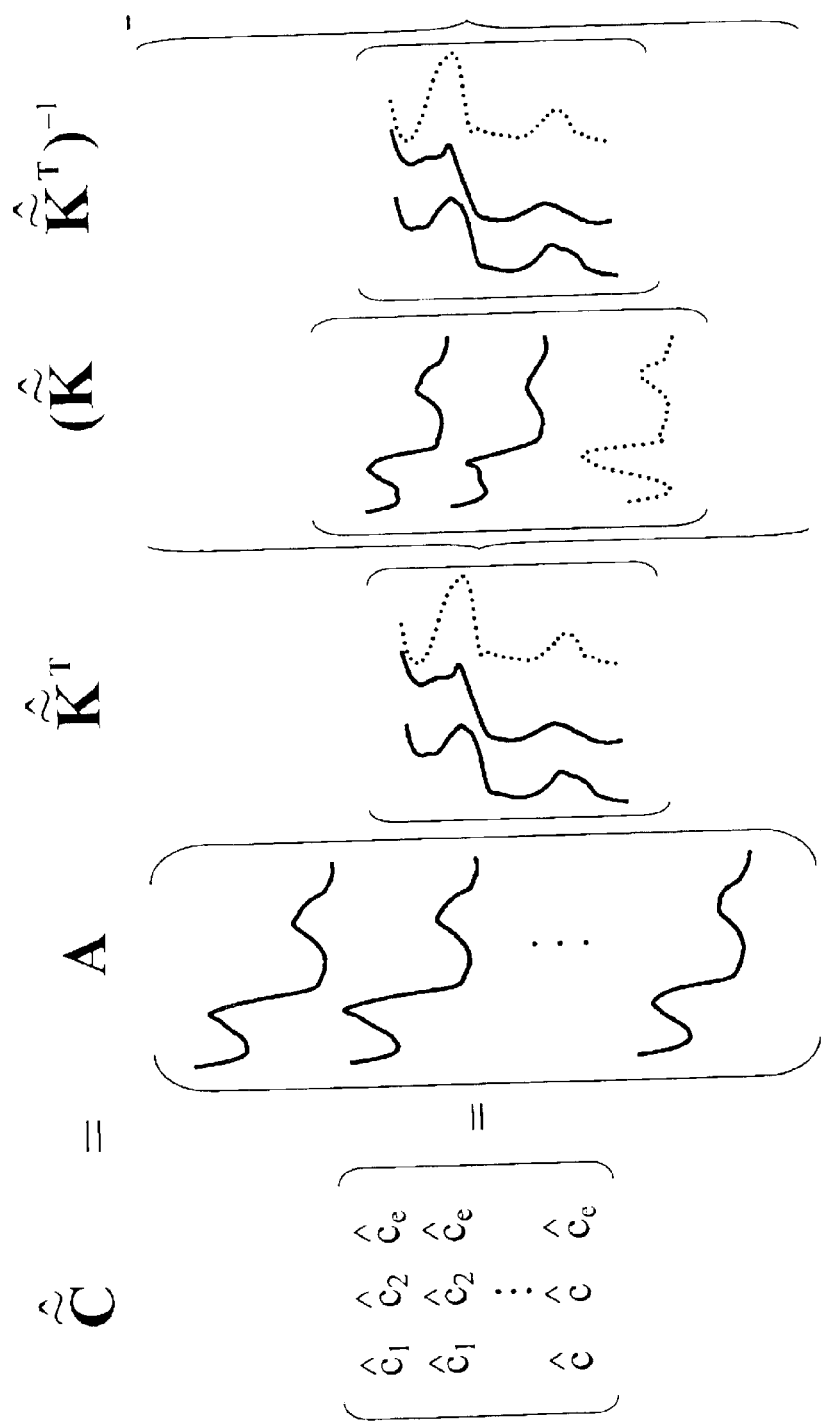
FIG. 2 depicts pictorially Eq. (17).

To better understand the present invention, the following introductory discussion is provided. The notation in the equations below uses upper-case bold letters for matrices, lower-case bold letters for vectors, and italicized letters for scalars. We use the $\wedge$ to indicate estimated values, $^T$ to denote a transposed matrix, $^{-1}$ for matrix inversion, $^+$ for the pseudoinverse of a matrix, and for augmented matrices. The use of the pseudoinverse can result in improved numerical precision from a variety of methods, e.g. singular value decomposition. Vectors are column vectors with row vectors indicated by the transpose of the vector.

As used herein, the term multivariate spectral data includes all types of multivariate data (i.e., data related to each sample or object is composed of responses from two or more variables). As used herein, spectral data to be used in the multivariate spectral analysis are considered to be any form of data where there are responses at two or more measured variables (e.g., wavelength, time, retention time, frequency, etc.) due to one or more perturbation sources (e.g., electromagnetic radiation, vibration, temperature, mechanical impulses, etc.). Therefore, the present invention can be applied to conventional spectroscopic methods that include, but are not limited to, infrared, near-infrared, visible, ultraviolet, X-ray, gamma-ray, Raman, mass spectroscopy, ion-mobility mass spectroscopy, Auger, fluorescence, phosphorescence, ESCA, far-infrared, microwave, x-ray fluorescence, NMR, energy loss spectroscopy, EDAX, ESR, and multi- and hyper-spectral imaging spectroscopy. These spectroscopic methods can be used in absorption, transmission, reflection, or emission modes. In addition, the methods of the present invention can be applied to other forms of multivariate data that include, but are not limited to, seismic data, chromatographic data, thermal gravimetric analysis, image data, and responses from multiple sensors. In particular, the methods of the present invention can be used to provide quantitative analysis of image data of the type provided with recently available commercial hyper-spectral imaging spectrometers. The methods can also be applied to the analysis of multispectral and hyperspectral image data obtained from remote sensors, such as satellite or airborne hyperspectral imaging sensors.

Classical Least Squares

The basic CLS method can be described by the following relationship:

$$A = CK + E_A \tag{1}$$

where A is a n×p matrix of measured spectra from n calibration samples at p frequencies, C is a n×m matrix of reference component values for each of the m spectrally active components, K is a m×p matrix of in situ pure-component spectra scaled to unit concentration and pathlength for each component m, and $E_A$ is a n×p matrix of spectral residuals (i.e., model errors, if the model is not linear or if K does not include all the pure-component spectra, and spectral noise) for each frequency p. Although a component can typically be a chemical species and a component value can typically be a concentration of the chemical species, the term component as used herein generally applies to any source of spectral variation, be it chemical, physical or otherwise. Examples of sources of spectral variation that can be modeled include the effect of the individual chemical species, chemical interactions, or any changes caused by a wide variety of physical parameters which can induce spectral variations, such as temperature variations, spectrometer drift, humidity changes, and sample insertions. Note that the physical property of temperature can have a considerable quantifiable effect on the sample spectra as can be seen from samples containing an aqueous solvent. The CLS calibration step requires determining the least-squares estimate for pure component spectra from a set of calibration samples with known component values. These estimated pure-component spectra are given by:

$$\hat{K} = (C^T C)^{-1} C^T A = C^+ A \tag{2}$$

where C is the matrix of reference component values for the spectrally active components in the calibration sample set and A is the matrix of measured spectra for the calibration sample set.

In a CLS prediction step, the estimated pure-component spectra can then be used to predict the component values in an unknown set of samples according to:

$$\hat{C} = A_P \hat{K}^T (\hat{K}\hat{K}^T)^{-1} = A_P (\hat{K}^T)^+ \tag{3}$$

where now $A_P$ is the matrix of measured spectra for the unknown samples.

Eq. (2) provides accurate estimates of the known pure-component spectra $\hat{K}$, and therefore accurate predictions of the unknown component values $\hat{C}$, only if the data fit a linear model and C contains all the components that contribute to spectral variation in the calibration sample spectra A. The accuracy of the estimated pure-component spectra $\hat{K}$ improves with each additional known reference value $c_i$ added to the CLS model. Therefore, the present invention is most useful in analyzing multivariate spectral data when there are unmodeled sources of spectral variation in the calibration model.

Augmented Classical Least Squares

The present invention provides a family of methods for analyzing multivariate data where there are unmodeled sources of spectral variation in the calibration model. The family of methods can be broadly described as first obtaining reference variables for a set of calibration samples (e.g., reference spectral data and reference values for components in the set of calibration samples). An estimate is obtained for at least one of the reference variables for the set of calibration samples. Thereafter, a residual is obtained between the at least one reference variable and its corresponding estimated variable. The residual between the estimated and reference variables is used to augment its corresponding reference variable. Using the augmented reference variable, a value of at least one component in a set of unknown samples is predicted. Augmentation can be repeated until all sources of spectral variation are accounted for in the set of calibration samples. The iterative process allows the development of a CLS-type calibration model comparable in quantitative prediction ability to implicit multivariate calibration methods even when unmodeled spectrally active components are present in the calibration sample spectra. The present invention generates an adaptable model that can achieve excellent quantitative and qualitative prediction results for samples of unknown composition that contain unmodeled sources of spectral variation.

In the spectral-residual-augmented classical least squares (SRACLS) embodiment of the present invention, a spectral residual matrix $E_A$ can be determined from a CLS estimate of the pure-component spectra $\hat{K}$, reference values C, and calibration spectra A:

$$E_A = A - C\hat{K} \tag{4}$$

The rows of the estimated pure-component spectra $\hat{K}$ matrix can be augmented directly with all or selected vectors from the spectral residual matrix $E_A$ to correct the CLS model for unmodeled, spectrally active components. The augmented matrix $$\hat{\hat{K}}$$

can then be used in an augmented CLS prediction to obtain predicted component values $$\hat{\hat{C}}$$

for a prediction set of unknown samples:

$$\hat{\hat{C}} = A_P \hat{\hat{K}} \left( \hat{\hat{K}} \hat{\hat{K}}^T \right)^{-1} = A_P \hat{\hat{K}}^+ \tag{5}$$

where now $A_P$ represents the spectral matrix of the unknown samples to be predicted.

For an incompletely specified and/or nonlinear model, the spectral residual $E_A$ includes a set of correlated, non-uniform errors that can be further decomposed into a sum of correlated errors, due to unmodeled spectral components, nonlinearities, or system-related correlated errors; and uncorrelated random errors representing system noise and/or spectral variation that are not relevant to prediction.

Factor analysis methods can be applied to the spectral residual $E_A$ to separate the sources of these errors. Thus, the spectral residual $E_A$ can be described as:

$$E_A = TP + E \qquad (6)$$

where T and P are the set of n×r scores and r×p loading vectors, respectively, obtained from the factor analysis of the spectral residuals $E_A$, and E is the set of n×p random errors and spectral variations not useful for prediction. The dimension r is the rank of the spectral residual matrix $E_A$ or the number of factors that are required for optimal prediction. Therefore, Eq. (1) can be re-written as follows:

$$A = CK + TP + E \qquad (7)$$

In one embodiment of the present invention, Eq. (6) can be factor analyzed by any factor analysis method. Common methods include principal component analysis (PCA), partial least squares (PLS), or principal component regression (PCR). If PLS or PCR is used, then concentration errors (to be discussed later) will be included in the calibration process, as described in U.S. Pat. No. 6,341,257, which is incorporated herein by reference. The factor analysis can use either an orthogonal factor analysis method or any non-orthogonal factor analysis method.

Using only the spectral residuals in the factor analysis, the scores, T, or the loading vectors, P, can be used to augment the CLS calibration model. If PCA is used as the factor analysis method applied to the calibration spectral residuals $E_A$, then the eigenvectors, P (i.e., the rows of P), can augment the rows of the $\hat{K}$ matrix using the SRACLS model to improve the prediction ability of the CLS model. The augmented CLS prediction for component values $$\hat{\tilde{C}}$$

can then be obtained according to Eq. (5). Martens and Naes (*Multivariate Calibration*; John Wiley & Sons: Chichester 1989) suggested this approach for removing the effects of unmodeled components. However, Martens and Naes did not use the augmented pure-component spectra $$\hat{\tilde{K}}$$

in combination with a PACLS algorithm for prediction. When combined with PACLS (wherein spectral shapes obtained from data or information that are independent of the calibration data set can be used to update the spectral responses), the SRACLS model can be updated in a PACLS prediction step for the presence of unmodeled changes in the responses of the prediction samples.

The scores T can also be used to correct the CLS calibration model for unknown spectral components. In this case, the columns of T can augment the column dimension of the component values C matrix to form an augmented component value matrix $\tilde{C}$. Re-calibrating with the augmented CLS method as in Eq. (8) results in an augmented $$\hat{\tilde{K}}$$

matrix that allows the augmented CLS model to have better predictive properties than the original CLS model:

$$\hat{\tilde{K}} = (\tilde{C}^T \tilde{C})^{-1} \tilde{C}^T A \approx \tilde{C}^+ A \qquad (8)$$

When augmentation makes use of scores, this embodiment is referred to as scores-augmented classical least squares (SACLS). Indeed, one can also simply augment the component values C matrix with one or more columns of random numbers. In general, any set of vectors of the correct dimension for T can be used to improve the CLS model as long as they each contain some independent information relative to themselves or the original C matrix, i.e., they cannot be collinear with each other or C.

With both SRACLS and SACLS, the spectral residuals $E_A$ can be obtained from the full calibration model or from cross-validated calibrations. The optimal number of augmentations in either SRACLS of SACLS can be selected based on an F-test of the concentration residuals (using cross-validated concentration residuals) according to methods described by Haaland and Thomas, *Anal. Chem.* 60, 1193 (1988) and Haaland and Thomas, *Anal. Chem.* 60, 1202 (1988), both of which are incorporated herein by reference.

Another ACLS method involves the use of component value residuals $E_C$ (e.g., concentration residuals) to augment the component matrix C. When augmentation makes use of concentration residuals, the method is referred to as concentration-residual-augmented classical least squares (CRACLS). In general, each estimated pure-component spectrum will consist of the pure-component spectrum at unit reference value for the corresponding known reference component in C plus linear combinations of the unmodeled pure-component spectra, i.e.

$$\hat{k}_j = k_j + \sum_{i=0}^{m^u} b_i k_i^u \qquad (9)$$

where $\hat{k}_j$ represents the estimated pure-component spectrum for the $j^{th}$ component and $b_i$ are the linear scale factors for the $m^u$ unmodeled pure-component spectra $k_i^u$. In the CRACLS method, these estimated pure-component spectra $\hat{k}_j$ can then be used to estimate the reference component values $\hat{C}$ as follows:

$$\hat{C} = A\hat{K}^T(\hat{K}\hat{K}^T)^{-1} = A(\hat{K}^T)^+ \qquad (10)$$

An n×m component residuals matrix, $E_C$, then is given by:

$$E_C = \hat{C} - C \qquad (11)$$

The component residuals $E_C$ can be obtained from the entire set of calibration data after the CLS steps in Eqs. (9) and (10). Alternatively, the component residuals can be obtained from cross-validated predictions on calibration samples rotated out during the cross-validation procedure or from prediction on a set of validation samples that are not part of the calibration set.

To account for baseline variations, $\hat{K}$ can be augmented with explicit baseline functions, i.e., vectors representing the potential variations in baselines in the spectra. These baseline functions can include an offset, general polynomials, orthogonal Legendre polynomials, or any expected functional form of the baselines. A row is added to $\hat{K}$ for each additional order in the baseline function added. Using the PACLS technique, estimated or measured spectral shapes for other spectrally active components can be added to $\hat{K}$ as well. A corresponding column must be added to $\hat{C}$ for each added row in $\hat{K}$ before solving Eq. (10). If rows have been added to $\hat{K}$, then $E_C$ is computed using only the estimated reference values corresponding to the original reference values in C.

To consider unmodeled sources of spectral variation, Eq. (1) can be rewritten:

$$A = CK + C_u K_u + E \tag{12}$$

where $C_u$ is an n×m″ matrix that represents the unknown component values for each of the m″ unmodeled pure-component spectra in $K_u$, and E represents the error remaining after removing m″ unmodeled linear spectral effects. Even if $E_A$ in Eq. (1) is the result of nonlinear factors, the nonlinearities can be estimated by a linear approximation in $C_u K_u$, so even in those cases, E can be considerably smaller then $E_A$.

The matrix, $K_u$, can be decomposed into the sum of two terms. One part of $K_u$ can be written as the projection of $K_u$ onto the space spanned by K, (i.e., $P(K)K_u = DK$), where D is a m″×m matrix and m″ is the number of rows in $K_u$ and m is the number of rows in K. Another part of the decomposition of $K_u$ is orthogonal to K, denoted by G. The decomposition of $K_u$ is then:

$$K_u = DK + G \tag{13}$$

Substituting Eq. (13) into Eq. (12) and gathering terms yields:

$$A = (C + C_u D)K + C_u G + E \tag{14}$$

The estimated component values $\hat{C}$ in Eq. (10) are then approximately equal to $(C + C_u D)$. Consequently from Eq. (11), we have $$E_C \cong C_u D \tag{15}$$

Although D is not known, Eq. (15) still shows that each column, $e_c$, of $E_C$ approximates a linear combination of the unknown component values unless $K_u$ is orthogonal to K, (i.e., D=0, where 0 is the null matrix). However, if D=0, the unmodeled components will not contaminate the estimated component values $\hat{C}$ so they can be ignored without affecting the predicted component values.

In practice, D=0 will generally occur only if the spectral components do not overlap in the spectral region being analyzed. For calibration of the known components, the magnitudes for unit component value of the pure-component spectra for the unmodeled components are not required, since only the relative component values are needed to generate the correct net-analyte signals (NAS) for each of the known components. By including linear combinations of the unmodeled component values as additional columns in C and solving Eq. (16), the resulting additional pure-component spectra $$\hat{\tilde{K}}$$

will be linear combinations of the spectra of the unmodeled pure-components, $K_u$. When enough linear combinations are added to cover all sources of spectral variation beyond the noise, the NAS for each of the known components in $$\hat{\tilde{K}}$$

will be correct.

Selecting one vector of the component residuals, $e_c$, and augmenting the original C matrix with the selected residual vector $e_c$ as a new column creates the augmented n×(m+1) matrix, $\tilde{C}$. If there are more than one unmodeled spectrally active components, only one of the component residual vectors $e_c$, is used in the augmentation, since the residuals for the other unmodeled components will contain redundant information. Criteria for selecting which component residual vector $e_c$ to use will be discussed in more detail below.

Using $\tilde{C}$, the augmented, (m+1)×p, pure-component spectra matrix $$\hat{\tilde{K}}$$

can be computed according to:

$$\hat{\tilde{K}} = (\tilde{C}^T \tilde{C})^{-1} \tilde{C}^T A = \tilde{C}^+ A \tag{16}$$

This step of the CRACLS method is illustrated in FIG. 1 where the component residual vector $e_c$ used to augment the reference component value matrix C are given as the $e_i$'s, and the additional estimated pure-component spectrum in Eq. (16), is represented by the dotted line.

By iteration, additional augmentations can be used to remove additional unmodeled sources of spectral variation. The new augmented estimated pure-component spectra $$\hat{\tilde{K}}$$

from Eq. (16) can then be used to again estimate reference component values $$\hat{\tilde{C}}$$

for the calibration samples according to:

$$\hat{\tilde{C}} = A\hat{\tilde{K}}^T\left(\hat{\tilde{K}}\hat{\tilde{K}}^T\right)^{-1} = A(\hat{\tilde{K}}^T)^+ \tag{17}$$

where here A are the calibration spectra. This estimation step is shown in FIG. 2 where the $c_{ei}$'s represent the estimated component values for the additional pure-component spectrum (i.e., the dotted line). Since the additional spectrum is a linear combination of unspecified magnitude of the unmodeled pure-component spectra, the $c_{ei}$'s in $$\hat{\tilde{C}}$$

may not provide any useful quantitative information. A new n×m component residual matrix, $E_C'$, then is given by:

$$E_C' = \hat{C}' - C \tag{18}$$

where $\hat{C}'$ is an updated estimated component value matrix consisting only of the estimated component values in $$\hat{\tilde{C}}$$

corresponding to the known reference values in C.

The steps delineated by Eqs. (11, 16–17) remove one linear combination of the unmodeled spectral variations from the calibration model. These steps can be repeated again using one row from $E_C'$ to further augment the component value matrix. To mitigate all the additional sources of spectral variation (i.e., reduce the residual from $E_A$ in Eq. 1 to E in Eq. 14), these steps can be repeated for each of the independent sources of spectral variation present in the calibration data. In other words, the component residual vectors $e_c$, can span the space defined by the unmodeled spectrally active components. In all augmented CLS methods, the optimal number of augmentations can be determined using the same method for PLS factor selection that has been previously published for PLS and PCR. See, e.g., Haaland and Thomas, *Anal. Chem.* 60, 1193 (1988) and Haaland and Thomas, *Anal. Chem.* 60, 1202 (1988). In this factor or vector selection method, a maximum number of augmentations greater than the optimum number of augmentations is selected, and an ACLS model is determined for each level of augmentation up to this maximum number using cross-validation techniques. The optimal number of augmentations is then determined based on the F-test using cross-validated component residuals (from the full calibration model or from cross-validated calibration models) for each level of augmentation, similar to the procedure described by Haaland and Thomas. The component residuals $E_C$ in the CRACLS method can be generated from either the full models or the cross-validated models.

Using the fully augmented $\tilde{C}$, augmented pure-component spectra $$\hat{\tilde{K}}$$

can be calculated according to Eq. (16). This augmented pure-component spectral matrix $$\hat{\tilde{K}}$$

can then be used to predict component values $$\hat{\tilde{c}}$$

in the unknown samples according to Eq. (5).

Because any of the ACLS models represent a CLS-type model, they are well suited to take advantage of the newly developed PACLS technique. The PACLS algorithm further augments the augmented pure-component spectra $$\hat{\tilde{K}}$$

prior to prediction with spectral information representing unmodeled sources of spectral variation present in the unknown sample spectra to be predicted. Basically, $$\hat{\tilde{K}}$$

from the calibration model can be further augmented prior to the prediction step in Eq. (5) with more pure-component spectra that encompass spectrally active components in the prediction data set that were not present in the calibration model. The advantage of PACLS is that the calibration model can be updated quickly during prediction to account for new sources of spectral variation. Recomputing the calibration model using the original and the additional spectra, as required by the prior art, would take considerably more time.

The spectra added during prediction should account for all sources of spectral variation introduced during the collection of the prediction data that were not accounted for in the calibration model, as described in the previously referenced U.S. Pat. No. 6,415,233. If these sources of spectral variation can be attributed to a known component, a sample could be doped with the identified component to determine a spectral shape that can be added to the prediction. However, often the new sources of spectral variation (such as caused by instrument drift or sample insertion effects) cannot be so easily identified. Frequently, a repeat sample can be used to provide the required spectral information to augment the model for prediction. By repeatedly measuring a stable sample during calibration and prediction spectral measurements, spectral shapes for these new sources of spectral variation can be captured. The differences between repeated spectral measurements obtained during both calibration and prediction or an eigenvector analysis of those differences can provide the spectral information required for augmentation of the prediction model.

Note that, unlike PLS, the spectral variation can be incorporated using the PACLS method without knowing the values of various components. When using the repeat sample spectra, the assumption is that the spectra can be used to provide a reasonable estimate of the error covariance matrix, i.e., that the unmodeled sources of spectral variation affect the repeat sample spectra and the prediction sample spectra in the same way. This assumption is valid if the spectra are similar across all samples, which is the case for the dilute aqueous solutions considered herein. However, if the range of component values causes large variations in the sample spectra, it may be necessary to use a subset of repeat samples to adequately capture the impact of the unknown sources of spectral variation.

Figure 3A:
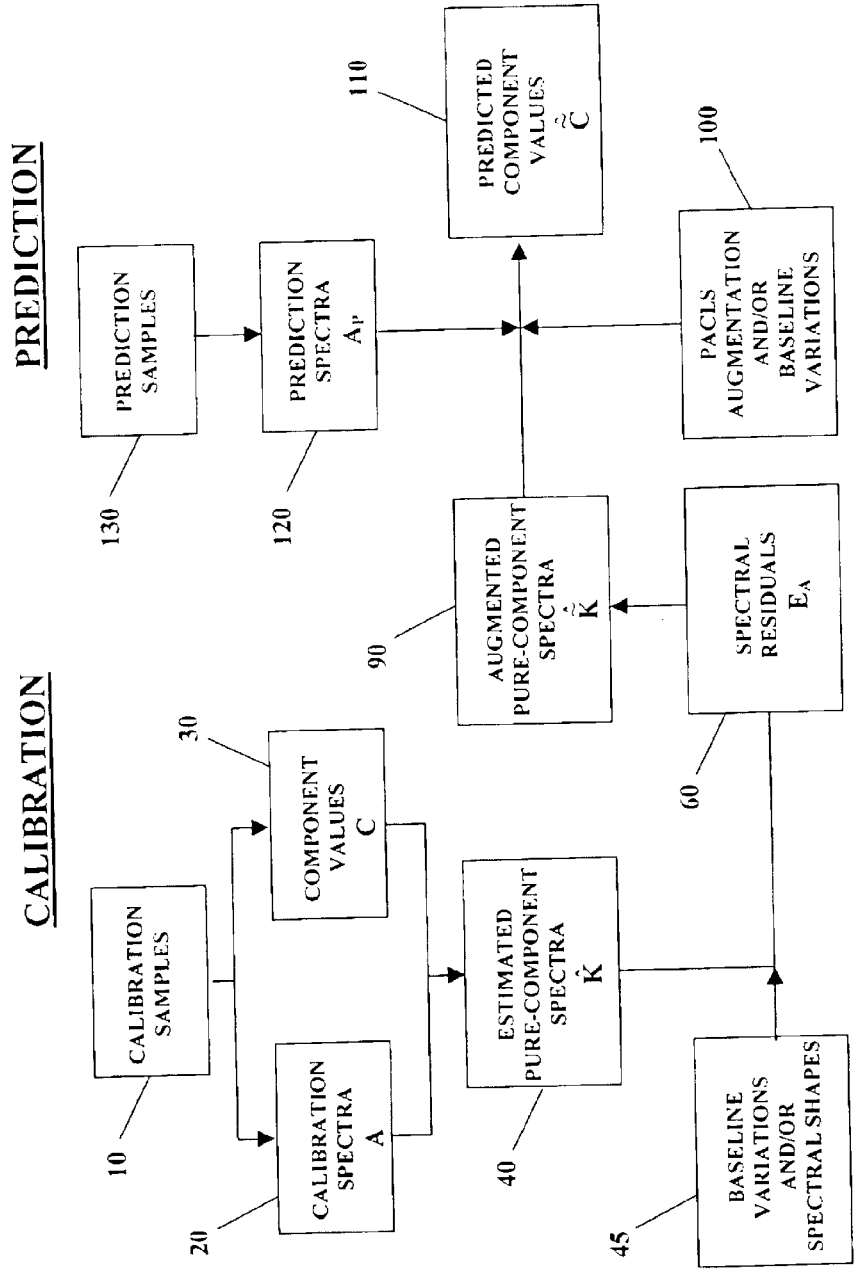
FIG. 3A is a flow diagram of the SRACLS embodiment of the present invention.

The following discussion of the SRACLS method of the present invention is made with reference to FIG. 3A. The present invention comprises two steps: calibration (steps 10–90) and prediction (steps 100–130).

Initially, a set of calibration samples containing a plurality of spectrally active components is obtained at 10. A set of calibration spectra A are obtained for some or all of the samples in the calibration sample set at 20. Additionally, a set of reference component values C is constructed for at least one of the spectrally active components in the calibration sample at 30. Such component values C typically provide a measure of the concentration of one or more known spectrally active component within the set of calibration samples. However, those skilled in the art will appreciate that such component values can represent other factors representative of the effects of both chemical and physical phenomenon that are spectrally active (i.e., can alter the spectral data such as temperature). With the calibration spectra A and component values C, Eq. (2) can be used at 40 to obtain CLS calibration model estimates of the pure-component spectra $\hat{K}$.

At step 45, baseline variations as well as estimated or measured spectral shapes representing other unmodeled components can be added to the estimated pure-component spectra $\hat{K}$.

At step 60, spectral residuals $E_A$ representative of the differences between the calibration spectra A and the estimated calibration spectra can be obtained according to Eq. (4) using the estimated pure-component spectra $\hat{K}$. The spectral residual matrix $E_A$ can be decomposed by factor analysis methods to separate the sources of the spectral residuals.

The spectral residuals can be decomposed per Eq. (6). All or selected spectral residual vectors from $E_A$ or P can be used to augment the rows of the estimated pure-component spectra $\hat{K}$ at 90 (i.e. to obtain augmented pure-component spectra $$\hat{\tilde{K}}$$

at least once or until all unmodeled, spectrally active components in the calibration sample set have been accounted for. Any of a variety of methods to using spectral or component value residuals, variation or other properties can be used to select the vectors for augmentation.

Figure 3B:
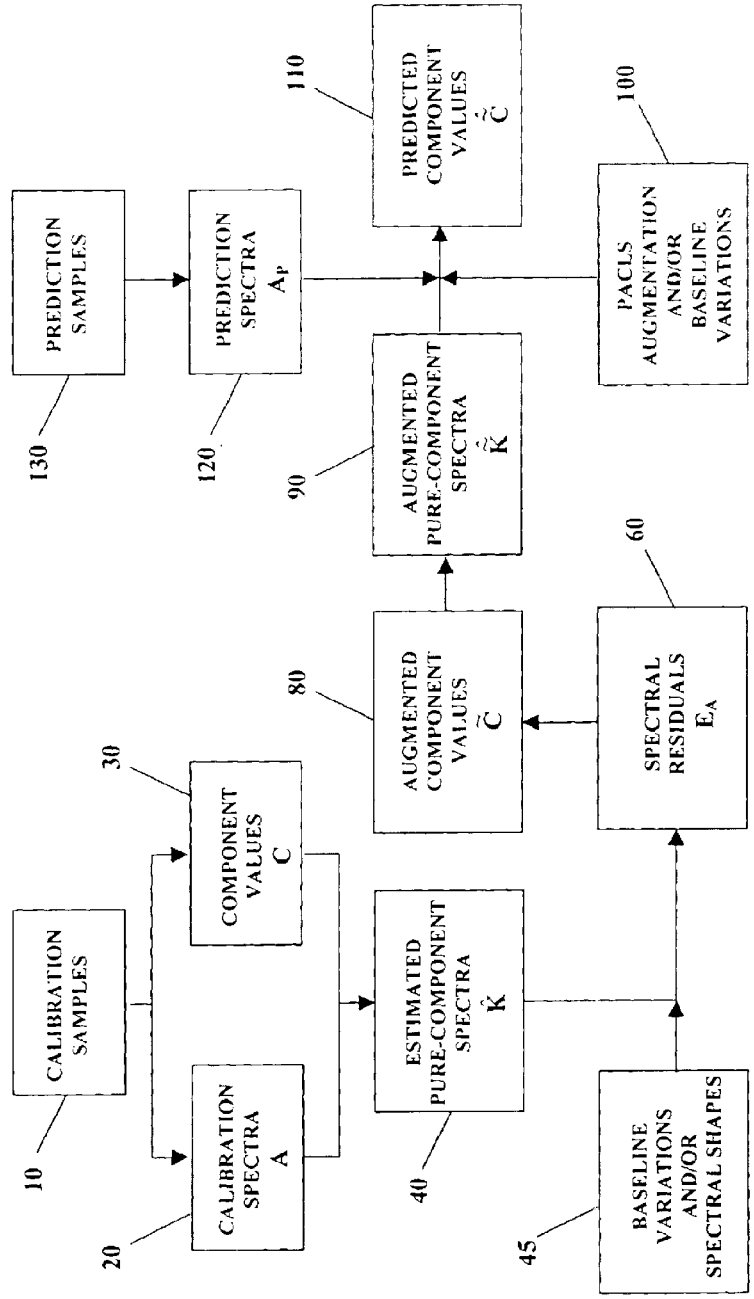
FIG. 3B is a flow diagram of the SACLS embodiment of the present invention.

In FIG. 3B is shown the SACLS method of the present invention. Here, the scores T can be used to correct the CLS model for unknown components. In this case, the columns of T can be added to C at 80 to augment the column dimension of C to form an augmented component value matrix $\tilde{C}$. Re-calibrating with this augmented CLS method as in Eq. (8) results in an augmented $$\hat{\tilde{K}}$$

matrix at step 90 that allows the augmented CLS calibration model to have better predictive properties than the original CLS model. All or selected score vectors can be added to C and the augmented CLS model recalibrated at least once or until all unmodeled, spectrally active components have been accounted for in the calibration set in the augmented pure-component matrix $$\hat{\tilde{K}}.$$

Any of a variety of methods can be used to select the scores for augmentation.

In FIGS. 3A and 3B, the augmented CLS prediction for component values $$\hat{\tilde{C}}$$

of the unknown samples then proceeds in the prediction steps 100–130. The SRACLS or SACLS estimate of the pure-component spectra $$\hat{\tilde{K}}$$

can be further augmented with spectral data using the PACLS technique (wherein spectral shapes obtained from data or information that are independent of the calibration sample set can be used to update the spectral responses) and/or with baseline variations at step 100. Thereafter, at step 110, a predicted component value matrix $$\hat{\tilde{C}}$$

for a prediction set of unknown samples 130 can be obtained according to Eq. (5), where now $A_P$ in step 120 is the matrix of the measured spectra for the unknown samples.

Figure 4:
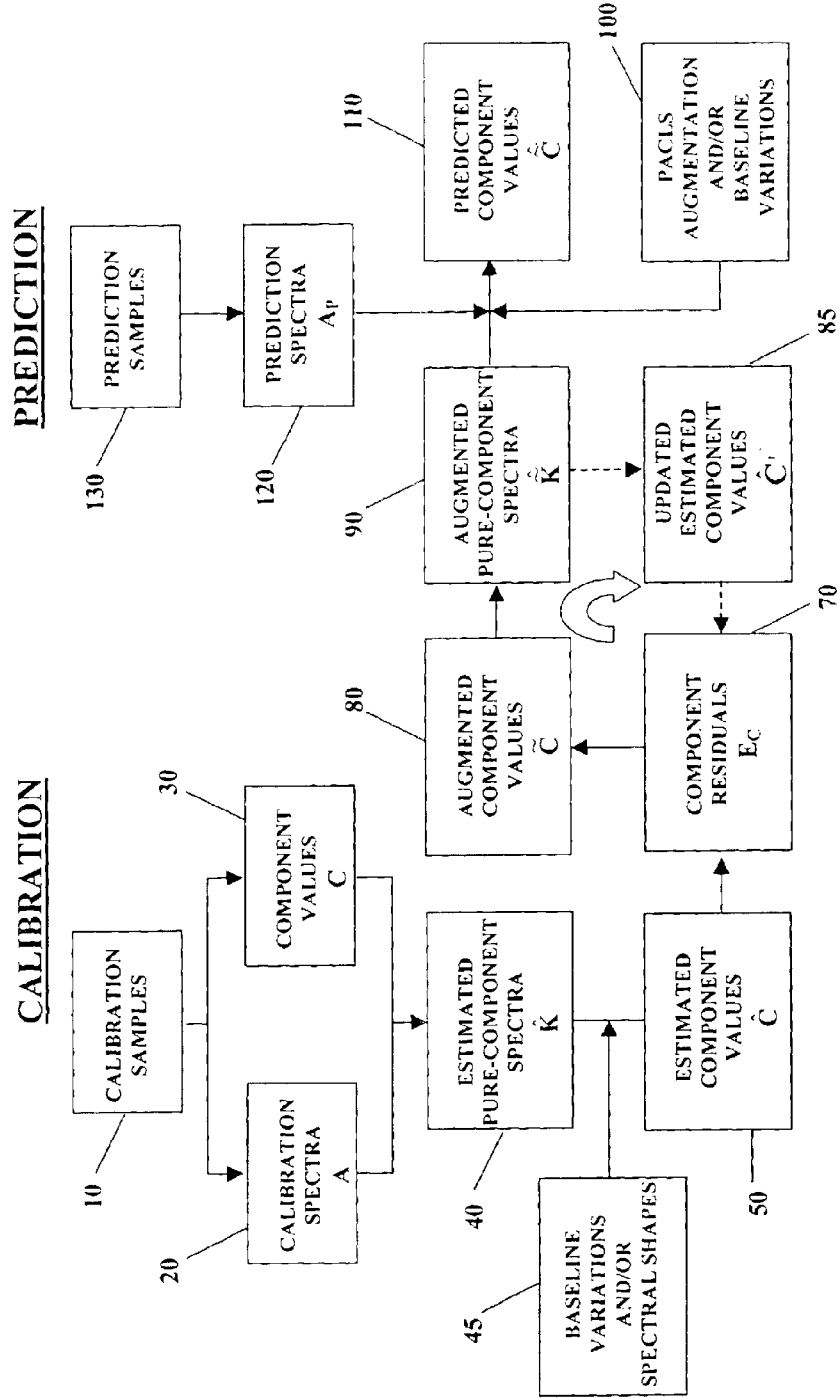
FIG. 4 is a flow diagram of the CRACLS embodiment of the present invention.

The following discussion of the CRACLS embodiment of the present invention is made with reference to FIG. 4. This embodiment also comprises two steps: calibration (steps 10–90) and prediction (steps 100–130).

Initially, a set of calibration samples containing a plurality of spectrally active components is obtained at 10. A set of calibration spectra A is obtained for some or all of the samples in the calibration sample set at 20. Additionally, a set of reference component values C is constructed for at least one of the spectrally active components in the calibration samples at 30. With the calibration spectra A and component values C, Eq. (2) can be used at 40 to obtain a CLS calibration model that comprises estimates of the pure-component spectra $\hat{K}$.

At step 45, baseline variations as well as estimated or measured spectral shapes representing unmodeled components can be added to the estimated pure-component spectra $\hat{K}$.

By extension at 50, an estimate of the component values $\hat{C}$ can be obtained with Eq. (10). At step 70, a component residual matrix $E_c$ representative of the differences between the estimated component values $\hat{C}$ and the reference component values C can be obtained according to Eq. (11). The component residual matrix $E_c$ can be decomposed into a component residual vector $e_c$, for each component included in the calibration.

Each component residual vector $e_c$, is representative of at least one unmodeled spectrally active component. A selected component residual vector $e_c$, can augment the original component values matrix C at 80 to form an augmented component values matrix $\tilde{C}$. Alternatively, a first estimate of the residual vector can simply be drawn from random numbers. The augmented component value matrix $\tilde{C}$ can be used to obtain an augmented estimate of the pure-component spectra $$\hat{\tilde{K}}$$

at step 90 according to Eq. (16). Using the singly augmented pure-component spectra $$\hat{\tilde{K}}$$

the CRACLS method can transition to prediction.

Alternatively, in another embodiment with iterations indicated by the circular arrow, steps 85–70–80–90 can be repeated to further augment the pure-component spectra $$\hat{\tilde{K}}$$

With iteration, an augmented component value matrix $$\hat{\tilde{C}},$$

is calculated according to Eq. (17), from which an updated estimated component value matrix $\hat{C}'$ can be obtained at step 85. This updated component value matrix $\hat{C}'$ can then be used to calculate a new component residual matrix $E_C'$ according to Eq. (18) at step 70. A selected component residual vector $e_c'$ can then be used to further augment the augmented component values matrix $\tilde{C}$ at step 80, from which a new augmented pure-component spectral matrix $$\hat{\tilde{K}}.$$

can be obtained at step 90. This iteration can be repeated until all unmodeled, spectrally active components in the calibration sample set have been accounted for.

After the desired number of augmentations, the augmented CLS prediction for component values $\hat{C}$ of the unknown samples then proceeds in the prediction steps 100–130. The estimate of the pure-component spectra $\hat{K}$ can be further augmented with spectral shapes representing spectrally active components in the prediction samples that where not modeled in calibration steps using the PACLS technique and/or with baseline variations at step 100. Thereafter, at step 110, a predicted component value matrix $\hat{C}$ for a prediction set of unknown samples 130 can be obtained according to Eq. (5), where now $A_P$ in step 120 is the matrix of the measured spectra for the unknown samples.

EXAMPLE 1

CRACLS Method Applied to the Analysis of Non-Imaging Data

The CRACLS method of the present invention is demonstrated with both simulated and real data derived from a system of dilute aqueous solutions containing glucose, ethanol, and urea. The simulated data demonstrate the effectiveness of the CRACLS algorithm and help to elucidate the principles behind the method. Using experimental data, the prediction abilities of CRACLS and PLS are compared during cross-validated calibration. In combination with PACLS, the CRACLS predictions are comparable to PLS for the prediction of the glucose, ethanol, and urea components for validation samples collected when significant instrument drift was also present.

The experimental samples consisted of a series of dilute aqueous solutions of glucose, ethanol, and urea each independently varied over the concentration range of 0–500 mg/dL. The samples were prepared by weight and volume in a pseudo D-optimal design that allowed each of the three analytes to be varied separately at 9 levels over the concentration range. The aqueous solvent was obtained from a single source of buffered saline solution. A detailed error analysis indicated that the samples were made to an accuracy of better than 1 mg/dL. The calibration data set consisted of 27 samples plus a repeat sample taken from the center of the design, i.e., the repeat sample contained approximately 250 mg/dL each of glucose, ethanol, and urea. The set of samples used for prediction (i.e., the validation samples) included the same repeat sample and 27 new samples from a design similar to the calibration set. The validation samples spanned the same 0 to 500 mg/dL concentration range for each of the analytes as in the calibration set. No sample from the new 27-sample prediction set had the same composition as any sample in the calibration set. Five of the prediction samples were removed from consideration when they were determined to be outlier samples contaminated by the epoxy used to seal the lids on the cuvettes.

The samples were sealed with a magnetic stirring bar in 10-mm pathlength cuvettes. A temperature controller propelled the magnetic stirrer while holding the samples at a temperature constant to 0.05° C. (±1 σ). The samples were placed in the temperature controller and held in the beam of the spectrometer for 4 minutes with stirring to allow the sample temperature to equilibrate. The near-infrared spectra of the samples were obtained on a Nicolet Model 750 Fourier transform infrared (FT-IR) spectrometer. The spectrometer employed a 75 W tungsten-halogen lamp, quartz beam splitter, and liquid-$N_2$-cooled InSb detector. Spectra at 16 $cm^{-1}$ resolution were obtained after averaging the interferograms over a 2-minute period.

The run order of the calibration sample set was randomized. The spectrum of the repeat sample held at 32° C. was obtained after each group of two calibration or prediction samples. The spectra for the prediction samples were obtained approximately one month after the calibration spectra were obtained. Purge variation was introduced during the prediction data set to induce additional short-term instrument drift and to accentuate the difficulty in maintaining the calibration. Sample temperature was varied in random order in 2° C. steps over the range of 30 to 34° C. for both the calibration and prediction samples. A background of the empty sample holder was obtained after each sample. Transmittance spectra of the calibration and validation sample sets were obtained by ratioing each single-beam sample spectrum to either its corresponding background or to the average of the background for the day. The spectra were then converted to absorbance. Since the best calibration and prediction results were obtained with the spectra obtained using the averaged daily background, only the results obtained from these spectra are described herein.

Simulated Data

To demonstrate the effectiveness of the present invention, a simulated spectral data set was constructed using pure-component spectra derived from experimental dilute aqueous data using standard CLS methods. While these simulated spectra do not precisely match the true pure-component spectra (primarily because of significant baseline variations resulting from spectrometer drift during the collection of the calibration spectra), they can be used to demonstrate the capabilities of the present invention. The simulated spectral data were constructed from these pure-component spectra and a series of assumed concentrations to generate two different sets of 25 samples, one for calibration and the other for validation, containing 0–500 mg/dL each of glucose, ethanol, and urea and 98000–100000 mg/dL of water. The sum of all the components from each sample was constrained to 100000. In addition, normally distributed random spectral noise was added to the absorbance spectra at a level of 0.3% of the maximum spectral absorbance intensity. This level of noise amounted to approximately 5% of the absorbance caused by the minor components, which is slightly more noise than we observed in the measured spectral data.

The spectral data were analyzed in the spectral region from 7500 to 11,000 $cm^{-1}$ using the CLS, PLS and CRACLS models. The calibration models for each technique were used for prediction of the validation sample spectra.

Figure 5:
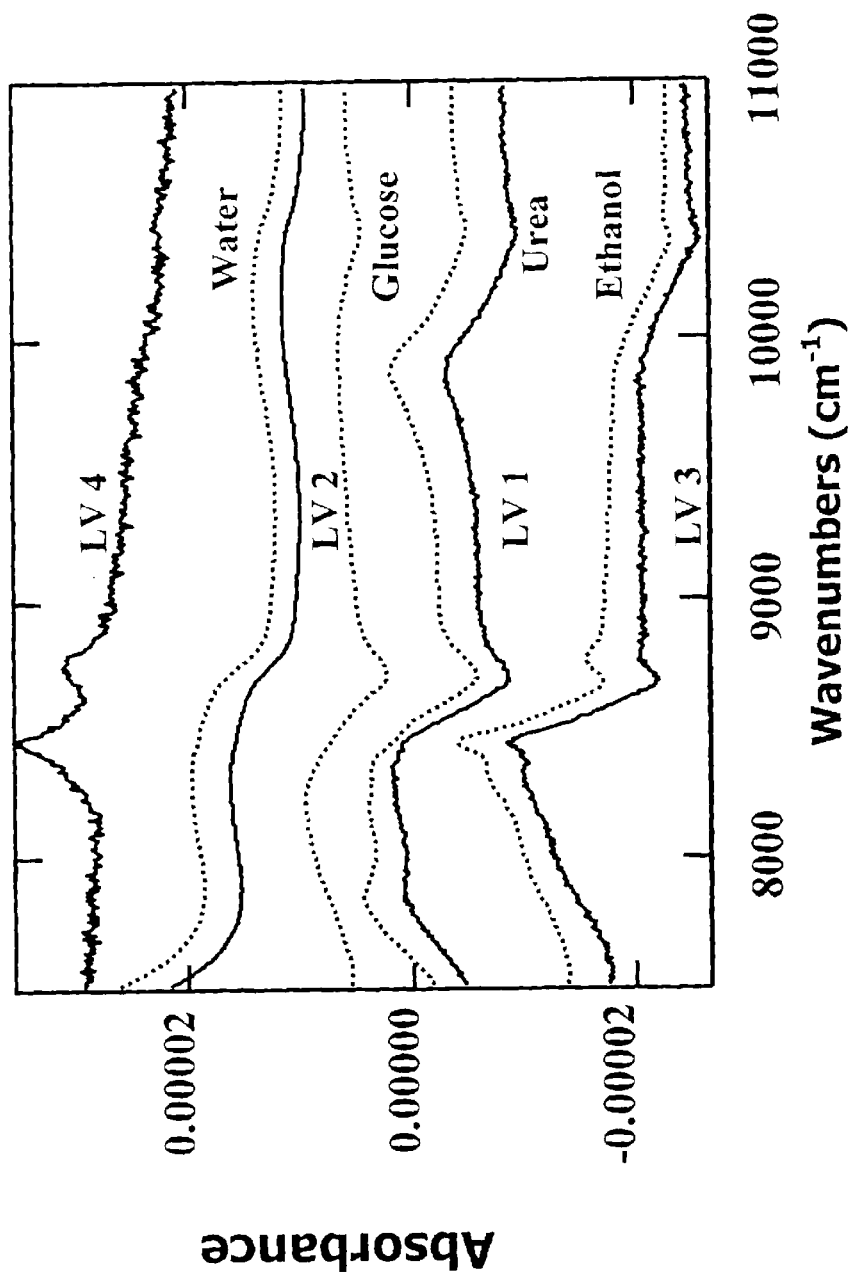
FIG. 5 depicts four loading vectors (solid lines) estimated from simulated spectra using the CRACLS calibration that includes urea and water concentrations and two concentration residual augmentations. The pure-component spectra (dotted lines) for water, glucose, urea, and ethanol are placed close to the corresponding loading vector (LV) for shape comparison.

The pure-component spectra K of the analytes and the water solvent used to generate the simulated spectral data are shown in FIG. 5. The glucose pure-component spectrum is similar to that of a modified water spectrum since glucose has no noticeable vibrational features of its own in this region of the spectrum. Rather, the CLS-estimated glucose spectrum is dominated by the interaction of glucose with the water solvent. Consequently, building a multivariate spectral model to estimate glucose concentration in the samples is more difficult than for the other analytes. On the other hand, both ethanol and urea have distinctive spectral features (e.g., at 8500 $cm^{-1}$ and 9900 $cm^{-1}$, respectively) so they are more easily quantified.

Figure 6:
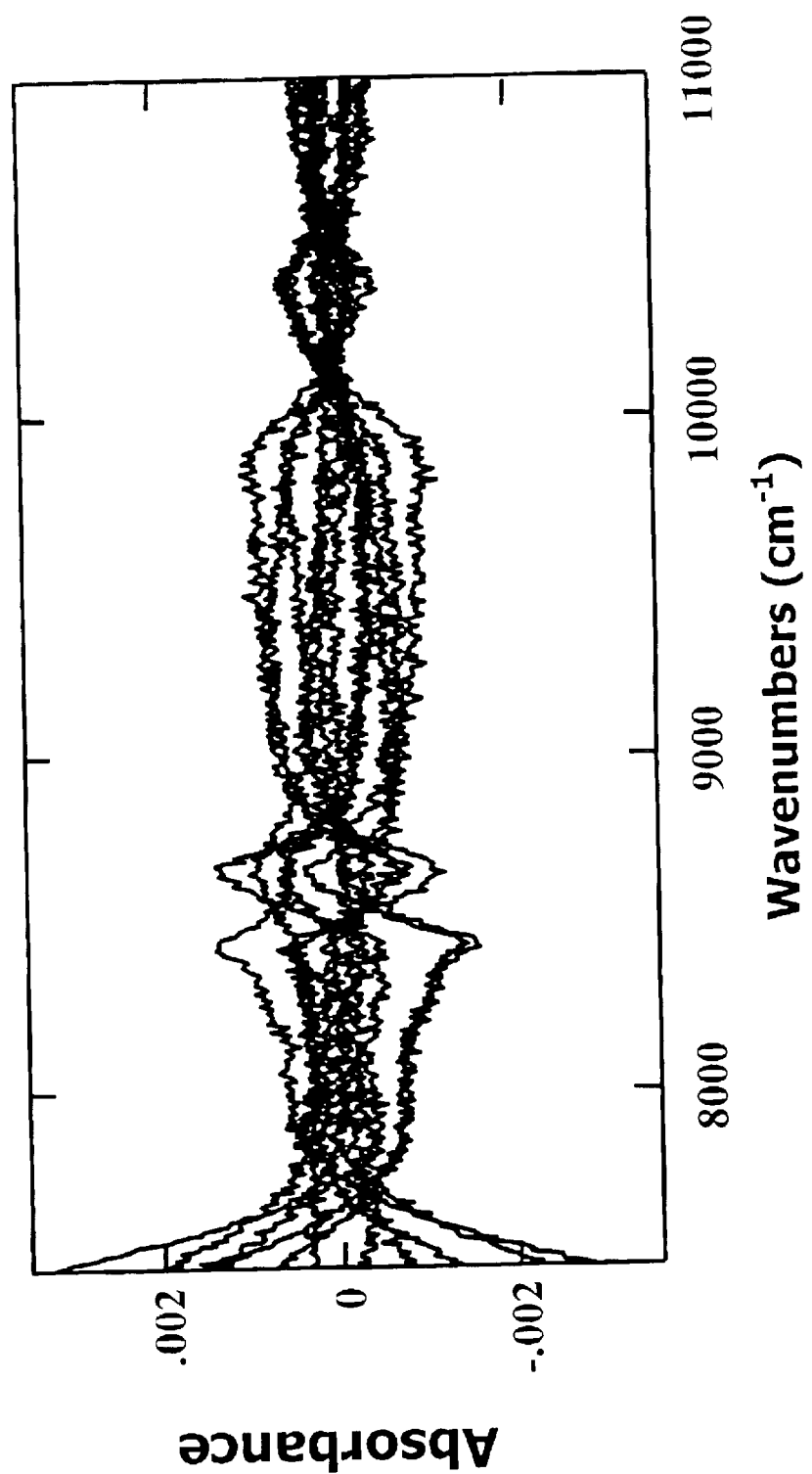
FIG. 6 depicts mean-centered simulated spectra showing high frequency noise.

Since water is the dominant component, the spectra of the simulated samples closely resemble that of water. However, if we remove the average spectrum, the spectral variation due to the analytes of each simulated sample is apparent as shown in FIG. 6. Most of the spectral variation shown is due to differences in the concentrations of the analytes between samples, which are accentuated by the baseline variations present in these pure-component spectra. The high-frequency component superimposed on the spectra is the added noise.

The effect of augmentation on the prediction ability of the CRACLS model was examined for the simulation samples. If only two of the four components, glucose and ethanol, are used to build a CLS model based on the simulated data, the cross-validated standard errors of prediction (CVSEP) for glucose and ethanol are 234 mg and 93 mg, respectively. That is, there is almost no prediction ability for glucose. However, if a CRACLS model is built, augmenting the calibration model with the concentration residuals twice, CVSEPs of 17 mg for glucose and 3 mg for ethanol are achieved, demonstrating that the present invention method has clear prediction ability for both components. If only one component's concentrations is included in the CRACLS calibration model, either glucose or ethanol, and the model is augmented three times, we get essentially the same CVSEPs as obtained as above. Adding the concentration residuals $E_c$ to the reference concentration matrix C successfully removed contamination of the unmodeled components from the calibration model for the included components.

The CRACLS loading vectors qualitatively resemble the pure-component spectra. The estimated pure-component spectra or loading vectors (LV) that resulted by including water and urea concentrations in the calibration and augmenting with concentration residuals twice are shown as the solid lines in FIG. 5. The vectors have been shifted slightly to show the comparisons more clearly with the pure-component spectra (the dotted lines). Also, the loading vector for ethanol was multiplied by −1 to match the orientation of the pure-component spectrum. The qualitative information of the loading vectors is apparent when compared with the actual pure-component shapes shown using the dotted lines. LV1 and LV2 closely resemble the pure-component spectra of the given components, urea and water, respectively. Also, even though ethanol was not included in the calibration, LV3 resembles its pure-component spectrum. Because the glucose has weak vibrational bands in this region, its spectral information is not apparent in any of the loading vectors, even in LV4.

If the major component is left out of the CLS calibration, the qualitative information will not be as apparent. The loading vectors will generally match the shape of the major component due to its overwhelming influence. The extent of this influence on the simulated data is shown by the decomposition of the vectors in the next section. With mean centering, the loading vectors obtained from a CLS calibration without the solvent concentrations will reveal more of the distinctive spectral features of the non-solvent components. However, for a mixture system where the sum of the concentrations is constrained to a constant, the CLS estimated pure-component analyte spectrum represents the net change in the sample spectrum due to a unit change in the analyte concentration. Consequently, the estimated pure-component spectrum will include negative spectral changes due to the displacement of the solvent that will contaminate the mean-centered loading vectors.

Figure 7:
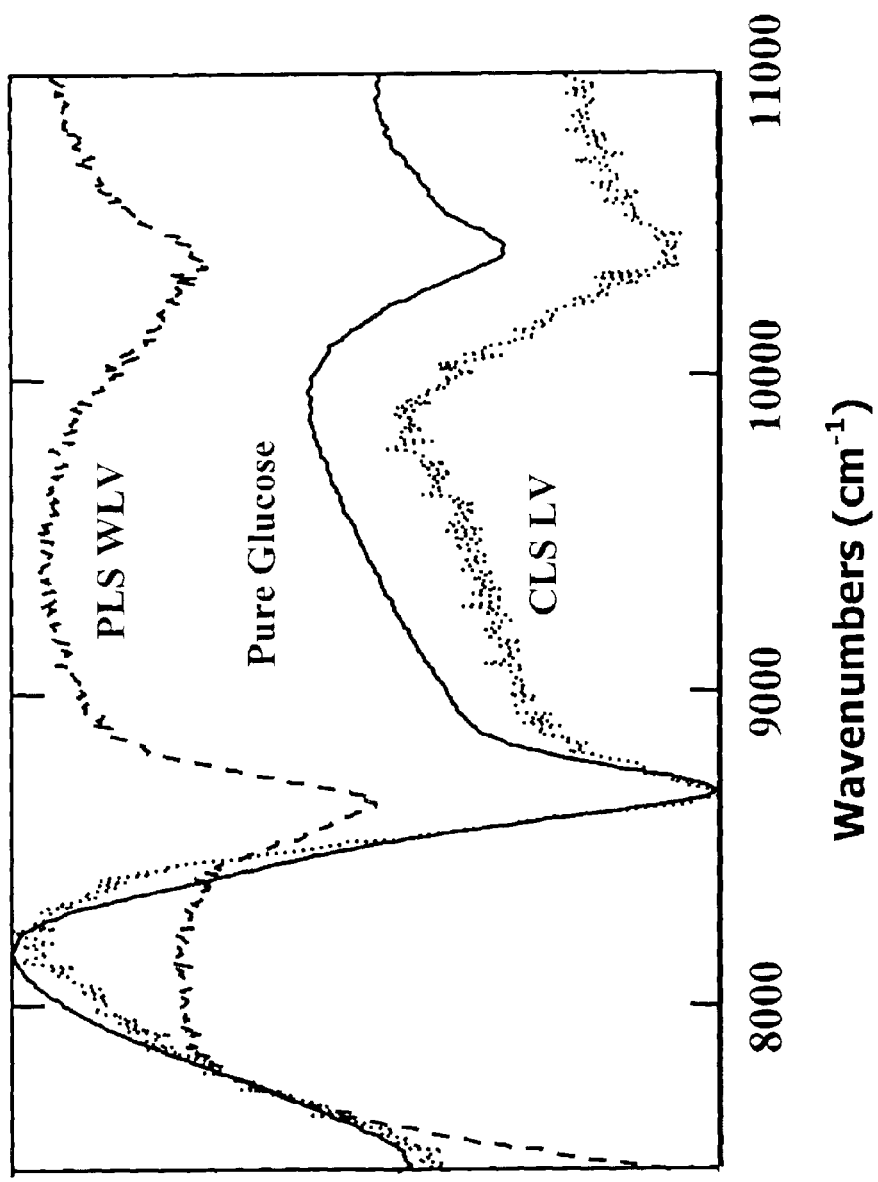
FIG. 7 depicts shape comparisons of the first weight loading vector (WLV) of a PLS glucose calibration and the first loading vector of a CLS calibration including glucose and water using the simulated data with the pure-component spectrum for glucose.

In every case, the qualitative information in the loading vectors for CLS will be equal to or better than PLS, since the first PLS weight-loading vector that retains the best qualitative information is generated from only one component. For CLS, and therefore for CRACLS, the qualitative information is improved as additional analyte concentrations are included in the calibration model. To illustrate this, a PLS calibration on glucose and a CLS calibration using only glucose and water were computed using the simulated data. The weight loading vector (WLV) from the PLS calibration and the loading vector (LV) from the CLS calibration for glucose are given in FIG. 7 as the dashed and dotted lines, respectively. The PLS weight loading vector is contaminated by the displacement of the water by the analyte, so the spectral shape does not match the pure-component shape (solid line) very well. The loading vector from a CLS calibration using only glucose and mean centering has the same shape. However, by including the water concentration, its contamination is removed, and the CLS first loading vector as shown in FIG. 7 provides an improved match to the pure-component spectrum. The more information included in the CLS calibration, the better the fit. If the spectrometer drift has a linear component, adding time of spectrum collection to the CLS concentration matrix will yield better pure-component spectra. Also CLS will generate better pure-component spectra than PLS when the known component concentrations are correlated.

The CRACLS loading vectors may be decomposed to demonstrate the effective removal of unmodeled sources of spectral variation, even if only the minor components are included in the calibration. The decomposition of the first four CRACLS loading vectors provides insight into this effectiveness when only the minor components of glucose and ethanol are included in the calibration without mean centering. By defining a CLS prediction model using all four true pure-component spectra with unit concentration, shown in FIG. 5, that were used to create the simulated data, the contribution of each of the true spectra to the loading vectors can be quantified as shown in Table I.

TABLE I

Quantity of pure-component spectra in CRACLS loading vectors using glucose and ethanol concentrations and two augmentations.

| | Glucose mg/dL | Ethanol mg/dL | Urea mg/dL | Water mg/dL |
|---|---|---|---|---|
| LV 1 | 1.0 | 0.0 | 0.4 | 196 |
| LV 2 | 0.0 | 1.0 | 0.5 | 134 |
| LV 3 | 0.0 | 0.0 | −0.1 | −150 |
| LV 4 | 0.0 | 0.0 | −1.0 | −48 |

The spectral residuals, after removing the given amount for each of the pure-component spectra, represent only random noise, indicating that all the spectral information contained in these loading vectors was removed. As shown in the Table I, the first and second loading vectors are the only ones that contain the glucose and ethanol pure-component spectra, respectively, corresponding to the order that their concentrations were placed in the concentration matrix. Note also that the pure-component spectra are present at unit concentration so they can provide quantitative information during prediction. In addition, the urea and water spectra contaminate these first two estimated pure-component spectra, as expected from Eq. (9).

In Table I, the amount of water far exceeds the other components, so all of the loading vector shapes are very similar to the pure water spectrum. The last two estimated pure-component spectra are linear combinations of only urea and water, the components left out of the concentration matrix. Consequently, during prediction using these four loading vectors, the resulting NAS for glucose and ethanol (i.e., the part of each pure-component spectrum orthogonal to all other vectors) is the same as obtained from the fully specified CLS model. Basically, the contamination of both water and urea is removed from the prediction of the glucose and ethanol by the third and fourth loading vectors. Therefore, the prediction model correctly determines the glucose and ethanol concentrations even though the concentrations for the other two components were not explicitly included in the calibration.

Results from the Experimental Data

Now we consider the experimental data. The mean calibration spectrum and the mean-centered calibration sample spectra are shown in FIGS. 8A and 8B, respectively. As with the simulated data, the water spectral features dominate the spectra before mean centering. However, most of the spectral variations in the mean-centered spectra shown in FIG. 8B are not due to concentration differences, but rather are the result of spectrometer drift and temperature variations. Due to these additional sources of variation, even a fully specified CLS model is not able to adequately model the data. This fact is clearly demonstrated in the CVSEPs from the full CLS model of the real calibration data shown in the first column of Table II.

TABLE II

Minor component CVSEPs for dilute aqueous solutions using CLS, PLS, and CRACLS calibration models.

|  | CLS | PLS[a] | CRACLS (10)[b] | CRACLS (15)[b] | CRACLS (20)[b] |
|---|---|---|---|---|---|
| Glucose (mg/dl) | 71 | 15 (11) | 18 | 16 | 15 |
| Ethanol (mg/dl) | 23 | 6 (11) | 6 | 5 | 5 |
| Urea (mg/dl) | 18 | 6 (9) | 6 | 5 | 5 |

[a]Value in parentheses is the optimal number of PLS factors used in the model.
[b]Values in parentheses represent the number of augmentations used in the CRACLS calibration.

All the chemical components and temperature were included in the model, and yet CLS still was unable to generate a precise calibration model. These results indicate why CLS is seldom used for prediction in multivariate calibrations. Also provided in Table II are the CVSEPs for PLS, with the optimum number of factors shown in parenthesis, and for CRACLS, using 10, 15 and 20 augmentations. Although there was a gradual decrease in the CVSEPs with more augmentations, the optimal number of augmentations was not apparent. Differences between the present invention calibration results and the PLS results for these data are not statistically significant.

To predict the validation data, information from the repeat sample was included in both the PLS and the CRACLS models. For PLS, all the spectra from the repeat sample taken with the prediction data set were added to the original calibration data set along with its component concentrations, and the PLS model was recalibrated. The cross-validated calibrations were performed initially by using the standard approach of removing all the data for each sample during the rotations (sample-out rotation), so that all the spectra for the repeat sample were removed at once. The number of loading vectors or factors for the PLS model was determined using an F-test on the cross-validated calibrations.

For the present invention, no changes were made in the CRACLS calibration model, i.e., no information from the repeat sample was given to the original CRACLS model to compute new pure-component spectra. Instead, the sources of spectral variation from the repeat sample shown in FIGS. 9A and 9B were used (without concentration information) to augment the pure-component matrix during prediction. The advantage of this PACLS augmentation is that the prediction model can be rapidly updated to account for new sources of spectral variation in the prediction data set. Recomputing the calibration model using the original and the additional spectra from the repeat sample would take considerably more computation time. The spectral difference between the average of the repeat spectra from the calibration and prediction data sets, shown in FIG. 9A, was added to the prediction model to capture the long-term spectrometer drift between the calibration and prediction days. Without the addition of this mean-difference spectrum, the predicted values show a definite bias. In addition, all the mean-centered repeat spectra for the prediction repeat sample, shown in FIG. 9B, were added to eliminate the detrimental effects of any short-term instrument drift during the collection of the prediction sample spectra.

By mean centering, the spectral contribution of the repeat sample's specific concentration is removed, leaving only the variation from non-chemical sources. Note the sharp features in the mean-centered spectra at approximately 8800 $cm^{-1}$ and 10600 $cm^{-1}$ in FIG. 9B. These features are the result of water vapor variations caused by the changes in the quality of the purge. Other less obvious spectrometer drift features contribute to the spectral variation as well. The background spectra are inadequate to correct for all sources of spectrometer drift. In fact, prediction results were best when an average background, rather than individual backgrounds, was used to obtain the absorbance spectra.

Table III shows the standard error of predictions (SEPs) for all the minor constituents in the prediction data set from various CLS, PLS and the present invention methods using calibration models based upon the calibration data set and the repeat sample information.

TABLE III

CVSEP for PLS and SEPs for CLS, PLS, and CRACLS on the prediction data set using models containing the repeat sample spectral information.

| Component | PLS | CLS | PLS-A[a] | PLS-B[a] | CRACLS/ PACLS(10)[b] | CRACLS/ PACLS(20)[b] |
|---|---|---|---|---|---|---|
| Glucose (mg/dl) | 18 | 287 | 55 (6) | 21 (12) | 19 | 19 |
| Ethanol (mg/dl) | 5 | 27 | 9 (8) | 4 (13) | 5 | 4 |
| Urea (mg/dl) | 5 | 42 | 4 (11) | 4 (12) | 4 | 4 |

[a]Value in parentheses is the optimal number of PLS factors used in the model.
[b]Values in parentheses represent the number of augmentations used in the CRACLS calibration.

As a comparison standard, the first column of Table III provides the CVSEP obtained from a separate PLS calibration obtained from the prediction data. As expected, CLS without the information about the interferents had poor prediction ability. PLS-A in Table III represents PLS recalibration with the optimal number of PLS factors selected during the sample-out cross-validated rotation. The results show that the model was inadequate, even though this method of rotating spectra out during cross-validation has generally been recommended to avoid overfitting the data.

Therefore, the cross-validated rotation was modified during recalibration so that each of the repeat spectra from the prediction set was rotated out one at a time (spectrum-out rotation). By using the spectrum-out cross-validated rotation, a more correct number of factors are selected, and the PLS-B model in Table III predicted well for these data. Cross-validated rotation removing individual spectra was preferred in this case over rotation removing all repeat spectra for a given sample since the repeat spectra were added to capture the system drift, not the component concentrations. By rotating all repeat spectra out at once, the F-test on the cross-validated calibrations did not adequately gauge the impact of the drift on the residuals for factor selection. While the spectra-out rotation worked better for this data set, it can lead to severe overfitting in other data sets. Adding several spectra for the same sample can over emphasize that sample in the model, which could lead to overfitting. Consequently, a careful analysis on a case-by-case basis is required to determine the appropriate type of spectral rotation during cross-validation for PLS. The proper choice of rotation for PLS will depend on the relative effects of the concentrations and the spectrometer drift or other sources of spectral variations that need to be modeled.

The results for present invention models using 10 and 20 augmentations during the CRACLS calibration are also presented in Table III. Again, it can be seen that the present invention compares favorably with PLS. Since the CRACLS model was developed using all components and the PLS model uses only one component at a time, it could be argued that the comparison is not valid. Therefore, the results were recalibrated using the present invention with 20 augmentations and the concentrations from only one component at a time to generate three separate models. Applying these models to the prediction data set, the SEPs for glucose, ethanol and urea were 20, 4, and 4 mg/dL, respectively. Essentially, these results matched the values derived when all the components were used in the CRACLS calibration model. Clearly, either way, the present invention method effectively removed the impact of all sources of spectral variation not represented by the given/known concentrations. Notice, however, that with CRACLS there is no problem with selecting a rotation method since the mean-centered repeat spectra are simply augmented to the estimated pure-component spectra during prediction.

When there is more than one known component, the concentration residual vector to use for augmentation needs to be chosen. To do this, the impact that the unmodeled components will have on each of the concentration residuals needs to be considered. From Eq. (15), the concentration residual vector is related to the projection of the unmodeled pure-component spectra, $K_u$, onto the space spanned by the modeled pure-component spectra, K, i.e. the portion of the unmodeled pure spectra that overlaps with the modeled pure spectra. If one of the unmodeled and one of the modeled pure-component spectra happen to be orthogonal, the concentration residual from that modeled component will not provide any information about the concentrations of the unmodeled component. However, in practice, orthogonal pure-component spectra rarely occur since orthogonality generally implies that there is no spectral overlap. Even using simulated data with pure-component spectra configured to be nearly orthogonal, augmentation with the concentration residual vector was still sufficient to produce a good predictive model.

Returning now to the simulation, to demonstrate the applicability of the various component residuals, a calibration model was developed using the simulated data, leaving out only the glucose concentrations during calibration. The concentration residuals vs. the reference concentration for the three components included in the calibration are shown in FIGS. 10A, 10B and 10C. The absolute value of the residuals varies from 20 to 100 mg/dL depending on the analyte. However, the pattern of the sample residuals for each of the components is basically the same, indicating that the contamination from glucose contributed approximately the same relative error to each of the samples for each of the components. Consequently, any of these component residuals will give statistically equivalent CRACLS models since the magnitude of the differences will only change the scaling factor of the estimated glucose pure-component spectrum corresponding to the augmented residual vector, $C_u$, in Eq. (15). The resulting NAS of the known components will be essentially identical regardless of which residual vector is selected.

Another choice for CRACLS is selection of the number of augmentations to use in the model. When using PLS, it is important to avoid using too many factors since overfitting the concentration data will degrade the prediction model. The excessive PLS factors have concentration residuals associated with them that can degrade the concentration predictions if they are included in the model. Finding the correct number of augmentations in CRACLS, however, may be less critical than choosing the optimal number of factors for PLS. Each additional loading vector generated by the concentration residual augmentation in CRACLS results in a reduction of the NASs for the analytes of interest. After the major unmodeled sources of spectral variation have been removed, the addition of more concentration residual vectors will generate estimated pure-component spectra that represent primarily random noise. Since random spectral noise is nearly orthogonal to the pure-component spectra of the known analytes, the impact on the NAS will be minimal. The insensitivity of CRACLS to the number of augmentations was demonstrated in the example above using real data. As shown in Tables II and III, the models generated using 10 or 20 augmentations gave equivalent results with no evidence of overfitting. A sufficient number of residual vectors need to be added to capture all of the unmodeled sources of spectral variation, but adding more residual vectors did not degrade the results. For these data, the CVSEPs for CRACLS dramatically decreased with increasing augmentations as real sources of spectral variation were modeled, and then the CVSEPs just gradually continued to decrease. The apparent insensitivity of CRACLS to the number of augmentations is an advantage over PLS since, at times, it is difficult to determine the optimal number of factors for PLS. The F-test for PLS can also be used on the cross-validated calibrations to select the number of augmentations in CRACLS. This F-test often results in selecting the maximum or near the maximum number of augmentations computed since the CVSEPs often just gradually decrease with each augmentation.

An important observation is that the PACLS-augmented prediction models are mathematically identical whether the estimated of measured spectral shapes representing additional unmodeled sources of spectral variation in the prediction data set are added to $\hat{K}$ of Eq. (10) during the cross validation in the calibration phase or to $$\hat{\hat{K}}$$

before performing prediction. In addition, equivalent prediction ability was achieved with CRACLS by using all the components simultaneously or by using the concentrations one component at a time. However, to enhance the sensitivity to outlier detection and to achieve better qualitative information in the estimated pure-component spectra, it is recommended to include all known reference concentrations in the cross-validated calibration.

EXAMPLE 2

ACLS Method Applied to the Analysis of Hyperspectral Image Data

Multivariate methods use a large number of spectral channels to take advantage of the signal averaging and resolving power inherent in spectral data. The multivariate nature of the spectra and the massive amount of data in hyperspectral images allow the characterization of systems with low signal-to-noise ratios and with multiple components whose spectral features overlap. Multivariate data also provide the opportunity to correct systematic spectral artifacts and aberrations introduced by the imaging instrument.

The quantitative analysis of hyperspectral image data collected from FT-IR imaging systems that employ focal plane array (FPA) detectors can be greatly hampered by the presence of system artifacts in the spectral and image data. Methods are required to eliminate the detrimental effects of these systematic artifacts if they cannot be eliminated experimentally. The characteristics of the systematic artifacts can be captured in the error covariance structure of the data estimated from repeat spectral image differences. By coupling the generalized ACLS method of the present invention with improved multivariate curve resolution (MCR) techniques and estimates of the error covariance structure of the data, the detrimental effects of the systematic artifacts present in hyperspectral imaging FT-IR systems can be greatly minimized.

MCR is a constrained alternating classical least squares method (alternating between CLS calibration and CLS prediction) used when the reference variables, such as pure-component spectra or component concentrations, are inadequately known for the standard CLS method. See R. Tauler et al., "Multivariate Curve Resolution Applied to Spectral Data from Multiple Runs of an Industrial Process," *Anal. Chem.* 65(15), 2040 (1993) and Bro and Dejong, "A fast non-negativity-constrained least squares algorithm," *J. of Chemometrics* 11(5), 393 (1997), both of which are incorporated herein by reference. Rather, MCR methods use constraints, such as non-negativity, equality, closure, monotonic constraint, unimodality, or selectivity, to achieve a solution. Therefore, MCR seeks to identify components of a data set by using alternating classical least squares to iteratively obtain solutions for each set of variables that putatively constitute the data. Because of the adaptability of the present invention and the fact that MCR employs a series of alternating classical least squares steps, ACLS methods can be readily added to the MCR algorithms to improve the component identification with such data sets.

Alternating Classical Least Squares

Conventional MCR methods start with a guess for either the K or C matrices, using random numbers or using other methods to arrive at a reasonable first guess, such as SIMPLISMA. See W. Windig and D. A. Stephenson, *Anal. Chem.* 64, 2735 (1992). If the starting guess is K, then CLS prediction is performed, with the appropriate constraint(s) applied (non-negativity, equality, etc.) to narrow the range of potential solutions, to provide a predicted component values matrix $\hat{C}$, according to:

$$\hat{C} = AK^T(KK^T)^{-1} = A(K^T)^+ \tag{19}$$

where A is the matrix of measured spectra for the unknown sample. Alternating to CLS calibration, estimated pure-component spectra $\hat{K}$ can then be obtained, again using constraints, according to:

$$\hat{K} = (\hat{C}^T\hat{C})^{-1}\hat{C}^T A = \hat{C}^+ A \tag{20}$$

The steps depicted by Eqs. (19) and (20) can be repeated, updating the pure-component spectra K in Eq. (19) for each iteration with new estimated pure-component spectra $\hat{K}$ from Eq. (20), and testing convergence according to:

$$\|A - \hat{C}\hat{K}\|^2 \tag{21}$$

until the set of iterations converges, minimizing the constrained classical least squares solution (i.e., a measure of the spectral residual $E_A$ is minimized).

Augmented Alternating Classical Least Squares

For any alternating least-squares MCR method, the calibration and prediction CLS steps can be augmented with information that it is desired for the least-squares fit to ignore (e.g., vectors representative of known or estimated spectral components or any estimate of the error covariance of the system). An estimate of the error covariance can be obtained, for example, by taking repeat spectra or, in the case of spectral imaging, repeat spectral images. Each least-squares calibration step in MCR iteration can be augmented by the scores obtained from the factor analysis of the error covariance matrix or each least-squares prediction step can be augmented by the loading vectors from the same matrix, or both steps can be augmented. Additional constraints can be applied to the non-augmented portion only of the augmented matrices. In this manner, quantitative analysis of spectral images can proceed without the need for standards even in the presence of large error covariance in the data. In general, ACLS methods will be useful in the analysis of any type of spectral data where estimates of the error covariance of the data can be obtained.

Figure 11:
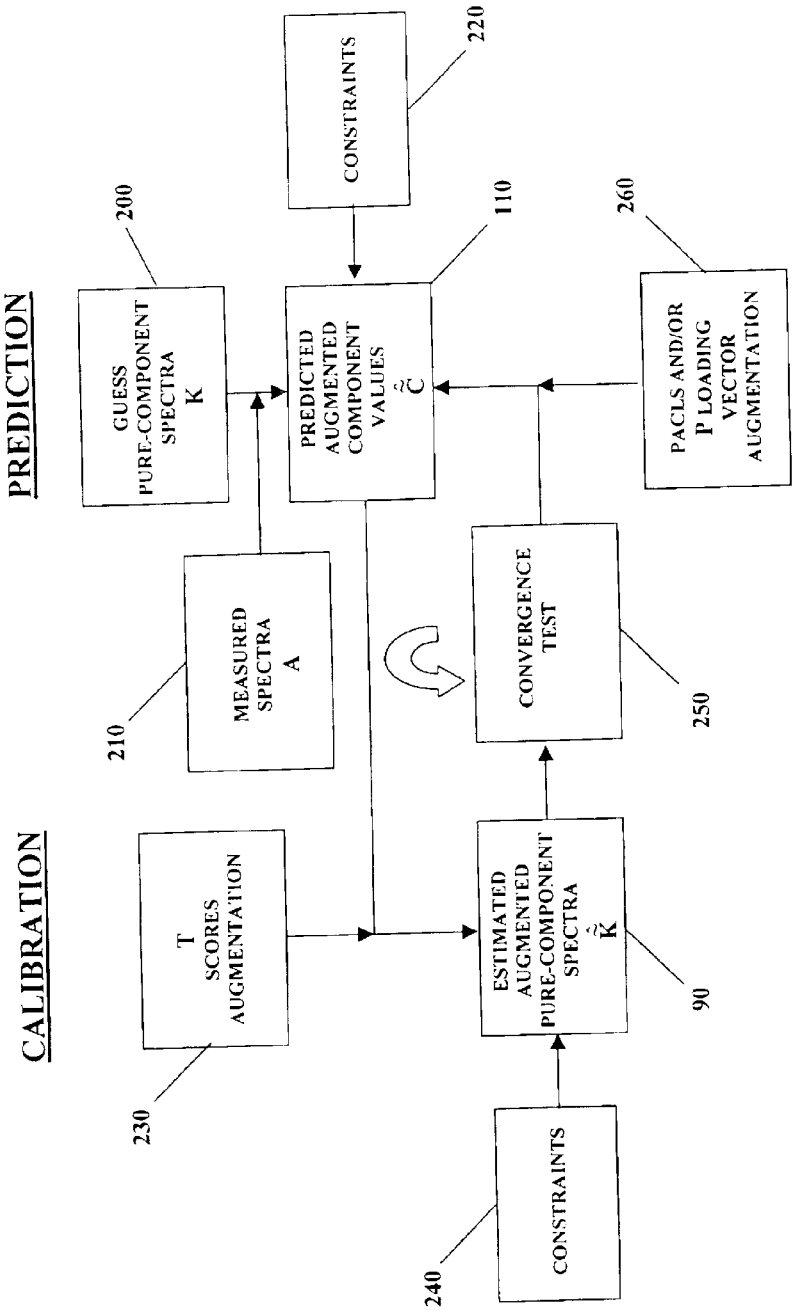
FIG. 11 is a flow diagram of the ACLS method of the present invention as applied to an alternating least squares model.

In FIG. 11 is shown an augmented alternating CLS embodiment of the present invention. A starting guess is made of the pure-component spectra K at step 200. This starting guess can also be a matrix of random numbers. In addition, an estimate of the error covariance $E_A$ of the measured spectra A is obtained. With spectral image data, this estimate of the error covariance $E_A$ can be obtained from the difference of repeat spectral images or from shift differences obtained from a single spectral image when repeat spectral images are not available. The estimate of the error covariance $E_A$ can then be factor analyzed into the product of T scores and P loading vectors. A preferred factor analysis method is PCA. The guessed pure-component spectra K can be augmented with one or more of the vectors of the P loading vectors at step 260 to obtain augmented pure-component spectra $\tilde{K}$. The guessed pure-component spectra K can also be augmented with one or more vectors representing spectral shapes that are representative of at least one additional source of spectral variation according to the PACLS method. A first set of augmented component values $$\hat{\tilde{C}}$$

can then be predicted at step 110 according to:

$$\hat{\tilde{C}} = A\tilde{K}^T(\tilde{K}\tilde{K}^T)^{-1} = A(\tilde{K}^T)^+ \tag{22}$$

where A is the matrix of measured spectra for the unknown sample from step 210. Additional constraints can be applied to the non-augmented portion of $$\hat{\tilde{C}}$$

at step 220. The first set of augmented component values $$\hat{\tilde{C}}$$

can be augmented with selected T scores at step 230 by replacing the augmented values in $$\hat{\tilde{C}}$$

with the appropriate scores from T to further improve the solution. An estimated augmented pure-component spectral matrix $\hat{\tilde{K}}$ can be obtained at step 90 according to:

$$\hat{\tilde{K}} = \left(\hat{\tilde{C}}^T \hat{\tilde{C}}\right)^{-1} \hat{\tilde{C}}^T \tilde{A} = \hat{\tilde{C}}^+ \tilde{A} \quad (23)$$

Constraints can be applied to the non-augmented portion of $\hat{\tilde{K}}$ at step 240 to further narrow the range of possible solutions. The first set of augmented component values $\hat{\tilde{C}}$ from step 110, or the replaced set of augmented component values $\hat{\tilde{C}}$ from step 230, and the estimated augmented pure-component spectra $\hat{\tilde{K}}$ from step 90 can then be used to test for convergence at step 250 according to:

$$\left\| \tilde{A} - \hat{\tilde{C}} \hat{\tilde{K}} \right\|^2 \quad (24)$$

These CLS prediction and calibration steps with constraints and augmentation can be repeated in a series of iterations indicated by the circular arrow until the set of iterations converges, minimizing the constrained augmented classical least squares solution. Alternatively, the initial guess can be C with the CLS calibration being performed first. The procedure is then similar to the above-described modified MCR method with only the starting point changing. These modified MCR methods can be applied to any set of multivariate data, and the use of augmented CLS methods is demonstrated below with spectroscopic image data.

To demonstrate the improvements possible with augmented CLS methods, the MCR analysis with augmentation were applied to a FT-IR spectral image obtained from a sample of neoprene thermally aged in air at elevated temperatures containing system artifacts in the image data. With the ACLS method applied to the spectral image data, augmentation with scores improved the pure-component spectral estimates while augmentation with the corresponding eigenvectors improved primarily the relative concentration maps predicted from the image data. Augmentation with both scores and loading vectors (eigenvectors) improved both the pure-component spectra and the concentration maps, even without the requirement for calibration standards.

Experimental

A sample of neoprene rubber was investigated. To obtain adequate signal to noise in the FT-IR image data, the neoprene sample did not contain the normal carbon filler found in many neoprene rubbers. The sample that was used to illustrate the methods of the present invention was obtained from a 2 mm×4 mm×4 mm block of neoprene that was aged for 6 days in an air furnace held at a temperature of 140° C. The sample was then potted in epoxy and the center of the sample was cut with a microtome to an approximate thickness of 15 $\mu$m. However, independent estimates of the sample thickness as a function of position on the sample indicated that the thickness varied by a factor of greater than three across the sample.

The spectrometer used in this study was a BioRad Stingray step-scan FT-IR imaging spectrometer equipped with a mercury-cadmium-telluride (MCT) FPA detector that had 4096 (64×64) detector elements. The sample was placed in the macro sampling compartment that provided a 4 mm×4 mm transmission image to be obtained of the thin 2 mm×4 mm aged neoprene sample. The sample was pressed flat onto a KBr window for support. Background single-beam images were obtained from a clear region of the KBr window next to the neoprene sample. Sample single-beam transmission image spectra were then obtained of the neoprene sample. The spectra were collected at a nominal spectral resolution of 16 cm$^{-1}$ using a step rate of 2.5 steps/sec and co-adding 64 images at each step of the interferometer. Data collection time was approximately 5 minutes for each spectral single-beam image. Three image spectra were obtained in rapid succession of the KBr window background before moving the sample into the beam. Three image spectra were then obtained from the neoprene sample without moving the sample. Two of these repeat image spectra were used to obtain an estimate of the error covariance structure of the data.

Analysis

The spectral data were collected with the use of the Bio-Rad Win-IR Pro software that came with the Stingray spectrometer. However, spectral analyses were performed using the Matlab code for the MCR, ACLS, and SIM-PLISMA algorithms.

Small numbers of spectra from each image were clear outliers and were removed from the analysis. These outliers generally exhibited spikes or steps in the raw interferograms. The sample images were trimmed to remove all pixels representing just the KBr window and mixed pixels at the extreme boundaries of the sample that contained sample and KBr window. Only pixels present in all single-beam images were retained for final analysis. The sample spectra were ratioed to backgrounds and converted to absorbance. Large, relatively complex baseline variations were present in these spectra. The presence of these baseline variations complicated attempts to extract pure-component spectra. Therefore, the spectra were preprocessed by isolating the spectral features of the sample and performing a separate linear baseline correction under each spectral band for each spectrum in the image.

When pathlength varies over the imaged area of the sample, concentration information can be confounded with pathlength changes, since pathlength and concentration changes are generally indistinguishable. These pathlength variations can be largely corrected if the Beers-Lambert law is closely followed and if a spectral region can be identified that represents only pathlength variations. Since the neoprene rubber sample thickness was not uniform over the sample area, pathlength corrections to the data were required to obtain meaningful concentration maps of the various components across the sample. To perform pathlength corrections without direct measurements of the sample thickness, a spectral band that was most representative of sample pathlength was identified. This band was selected among the six baseline-corrected bands by performing a principal components analysis (PCA) on each spectral band and examining the results carefully. Necessary conditions for a spectral band to be representative of sample pathlength are that the band be present in all pixels of the image, that it has a consistent spectral shape in all pixels, and that only multiplicative changes are present in the band. Spectral bands that fulfill these conditions of only a multiplicative change will have the first PCA eigenvector represent nearly all the variance, and the first eigenvector will have the same shape as the average spectrum of the selected band. Of the six bands identified in the neoprene sample, the 1440 cm$^{-1}$ band most nearly followed these criteria and was, therefore, selected as representing sample pathlength.

Once an appropriate spectral band has been selected for pathlength correction, pathlength correction terms can be determined for each spectrum in the hyperspectral image. Relative pathlength for each pixel was determined by assigning a relative pathlength of one to the average spectrum of the 1440 cm$^{-1}$ band and using the average spectrum in a CLS prediction of all sample image spectra. The CLS analysis also included a simultaneous fit of linear baseline components to the band. Relative pathlengths varied from 0.13 to 2.5. The thinnest pathlengths were at the edges of the sample. Because the spectra contained artifacts from the imaging system, the spectra were not scaled for pathlength since this process could serve to increase the variance of the artifact in the image. Rather, the MCR was performed on the uncorrected spectra, and the estimated concentrations were corrected for relative pathlength variations.

The primary goal of the analysis was to obtain the pure-component spectra and concentration maps of each component in the image directly from the spectral data, since standards were not available for these samples. As described above, quantitative analysis without standards can be accomplished with the MCR algorithm using constrained alternating least squares in an iterative process. Constraints were applied to limit the range of possible solutions in the analysis and minimize the detrimental effects of the system artifacts on the analyses. These constraints comprised both non-negativity of the concentrations and the pure-component spectra, since real concentrations and spectra will consist of all positive values, and equality constraints.

The MCR analysis requires a starting point for the pure spectra and/or their corresponding concentrations. In the analysis described herein, pure component spectra obtained from the SIMPLISMA algorithm were used as starting points. These pure-component spectra are generated by finding and extracting the purest spectral bands in the spectral data sets one at a time. From these purest pixels, often reasonable initial estimates of the pure-component spectra can be obtained. Random numbers can also be used as starting points.

Initially, MCR was performed starting with the SIMPLISMA estimated pure-component spectra using only non-negativity constraints. The constrained alternating least squares algorithm used was a modification of the fast non-negative least squares algorithm from the previously referenced Bro et al. Changes to Bro's algorithm were made to speed the convergence of the MCR analysis. The spectral data were heavily contaminated by systematic errors, probably due to readout problems from the FPA detector, that severely degraded the quality of the both the pure-component spectra and the concentration maps generated from the MCR analysis. The result is the presence of large correlated residuals in the spectral domain and a banding artifact in the concentration maps.

The standard method of applying MCR with non-negativity constraints to spectral data can be improved by augmentation of the calibration and prediction solutions with estimates of the error covariance structure in the spectra. All of the current implementations of the MCR algorithms assume that the spectral errors are random, of constant variance and independent (i.e., uncorrelated). These assumptions were violated in the FT-IR image data. The ACLS methods of the present invention enable the MCR analysis to be corrected for the presence of non-constant and correlated spectral errors in the data. To correct the MCR analysis using the ACLS methods, an estimate of the error covariance structure of the spectral image data is required. This estimate can be obtained from the repeat image spectral differences of the sample. If the sample does not move and does not change over time, then any changes in the image spectra at a given pixel are related to systematic changes in the system response as well as random noise.

In the past, $E_A$ in Eq. (1) has generally been assumed to consist of identically distributed uncorrelated errors of zero mean. However, instrument drift, system artifacts, and a variety of possible errors that occur in collecting the interferogram can generate correlated error structure. The conversion to absorbance also has the effect of generating errors with non-uniform error variance. The error covariance structure of $E_A$ has often been estimated in remote sensing applications with hyperspectral images with a shift difference generated from a single hyperspectral image. This shift difference assumes that the signal between pixels is slowly varying and, therefore, the spectral difference between adjacent pixels is representative of noise. The shift difference must be used if direct repeat image spectra cannot be obtained, for example in the case of a moving detector in remote sensing applications. However, in the laboratory, repeat image spectra can be obtained, and the difference between these images can be used to obtain an estimate of the error covariance structure of $E_A$. Since errors in the image data described herein are correlated, a PCA analysis of $E_A$ can serve to separate the correlated errors from the random error.

In Eq. (6), TP is the product of scores and eigenvectors from the PCA of $E_A$ for the r scores and eigenvectors that represent the significant correlated errors contained in $E_A$. The number of eigenvectors was selected based on a visual examination of the corresponding score images. Score images with nonrandom patterns were retained. E then contains primarily the random errors that are expected in any least squares analysis. To estimate C and K without the detrimental influence of T and P that can contaminate the concentration and pure-component spectral estimates, C can be augmented with T during calibration, or K can be augmented with P during prediction, or both. By augmenting columns of C with selected columns from T, the least squares estimate of K is forced to ignore any pattern in the image that has the same spatial distributions as any given set of column scores in the T vectors that are used to augment C. By augmenting the rows of K with selected rows from P, the least squares estimate of C is required to ignore any spectral shape contained in any given row eigenvector of P vectors that are used to augment K. The corresponding ACLS calibration and prediction equations that are part of the alternating least squares MCR procedure are then given by equations (22) and (23), respectively. In practice, the MCR method implements the augmentation by using equality constraints to force the estimates of K and C to ignore sources of spectral and spatial variation that are contained in the augmented $$\hat{C}$$

and $$\hat{K}$$

matrices.

Results from the Experimental Data

Figure 12:
FIG. 12 shows a video image of the thin neoprene sample aged for 6 days in air at 140° C.
Figure 13A:
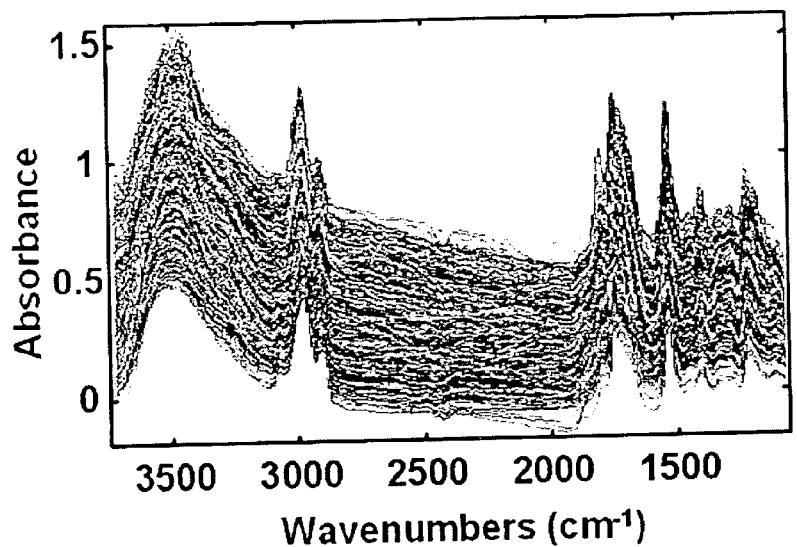
FIG. 13A depicts spectra of neoprene pixels from spectral image of the neoprene sample.

A visible video image of the approximate portion of the aged neoprene sample imaged by the FT-IR spectrometer is displayed in FIG. 12. A slight darkening from the center to the edge of the sample is the only indication in the visible image of the degradation of the sample due to the aging. The 1269 spectra from image pixels representing the sample are presented in FIG. 13A. Note that there are significant complex baseline variations present in these data. The spectra that were subjected to linear baseline correction for each of the six significant spectral bands of neoprene are presented in FIG. 13B. The preprocessed spectra in FIG. 13B were subjected to the MCR analysis.

As mentioned in the Experimental section, systematic artifacts were present in the FT-IR spectral image data. These artifacts were not always readily observable in the raw interferograms, single-beam spectra, or absorbance spectra. However, a PCA analysis of the spectral image data revealed the presence of the artifact as a systematic striped or banded pattern in the score images from the PCA analysis. As indicated in FIG. 14, this striped pattern was apparent in the PCA scores of interferograms, single-beams, and absorbance spectra obtained from the spectra of different sample or background images. The relative magnitude of the artifact varied considerably between various image data sets as evidenced by how many eigenvectors were generated before the artifact became noticeable. The data in FIG. 14 illustrates collected image data where the presence of the artifact varied from very small to significant as indicated by the fact that the striping artifact first becomes visible in factor 2, 5, or 10, depending on the image. To demonstrate the value of the ACLS methods applied to the MCR analysis, a spectral image where the artifact was a significant portion of the data was chosen.

Figure 15:
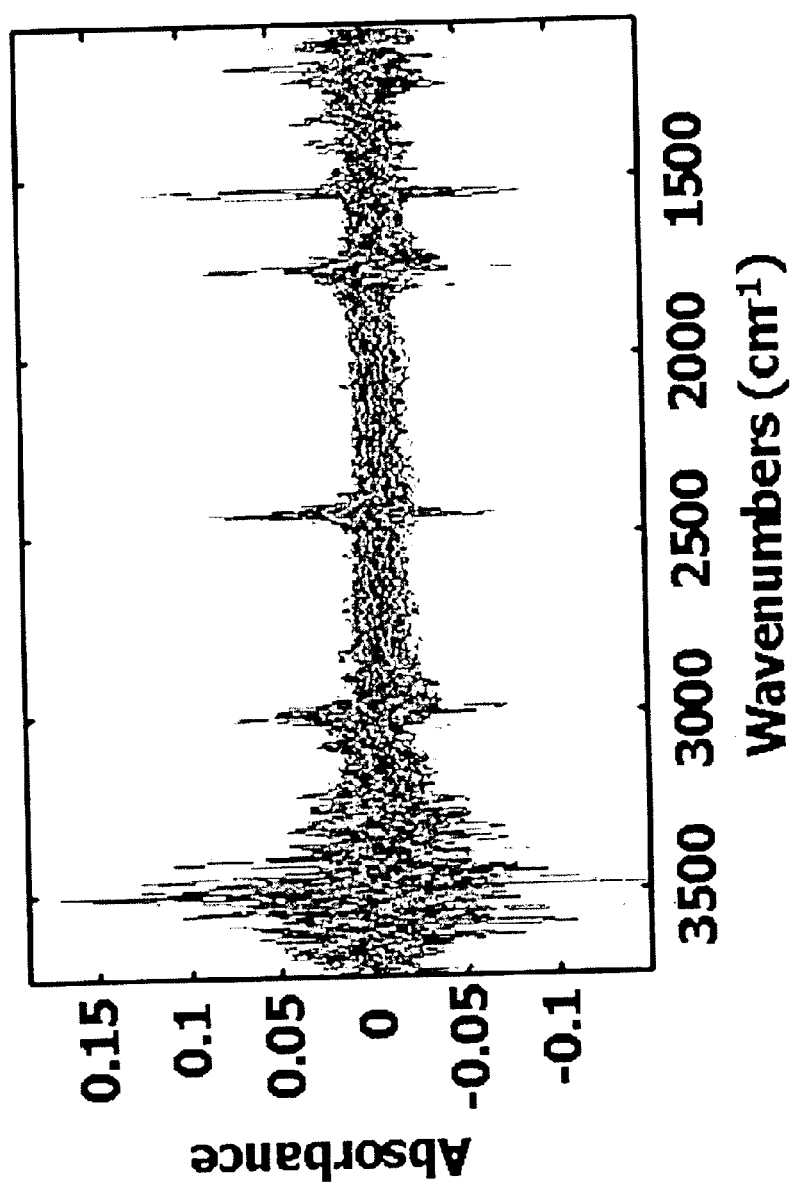
FIG. 15 depicts mean-centered repeat spectra from the neoprene pixels in the spectral image.

Not only is the artifact clearly present in the PCA score images, it is also present in the spectral data. In FIG. 15 are shown the mean-centered difference spectra between repeat images of the aged neoprene sample, in which the systematic error (noise) can be observed. Clearly, the noise in the difference spectra in FIG. 15 is not uniform. In fact, as expected by theory, the noise is higher in those regions where the absorbances are larger. Thus, the spectral noise is higher where the neoprene sample absorbs the IR beam. What is not clear from FIG. 15 is that the noise in the sample is also correlated between spectral frequencies. Thus, if the error is high at frequency p, it tends to be high at surrounding frequencies. The fact that the noise is high in broad spectral regions is not necessarily an indication of correlated error; it could simply be an indication that the noise is higher in broad spectral regions but uncorrelated between frequencies.

Figure 16:
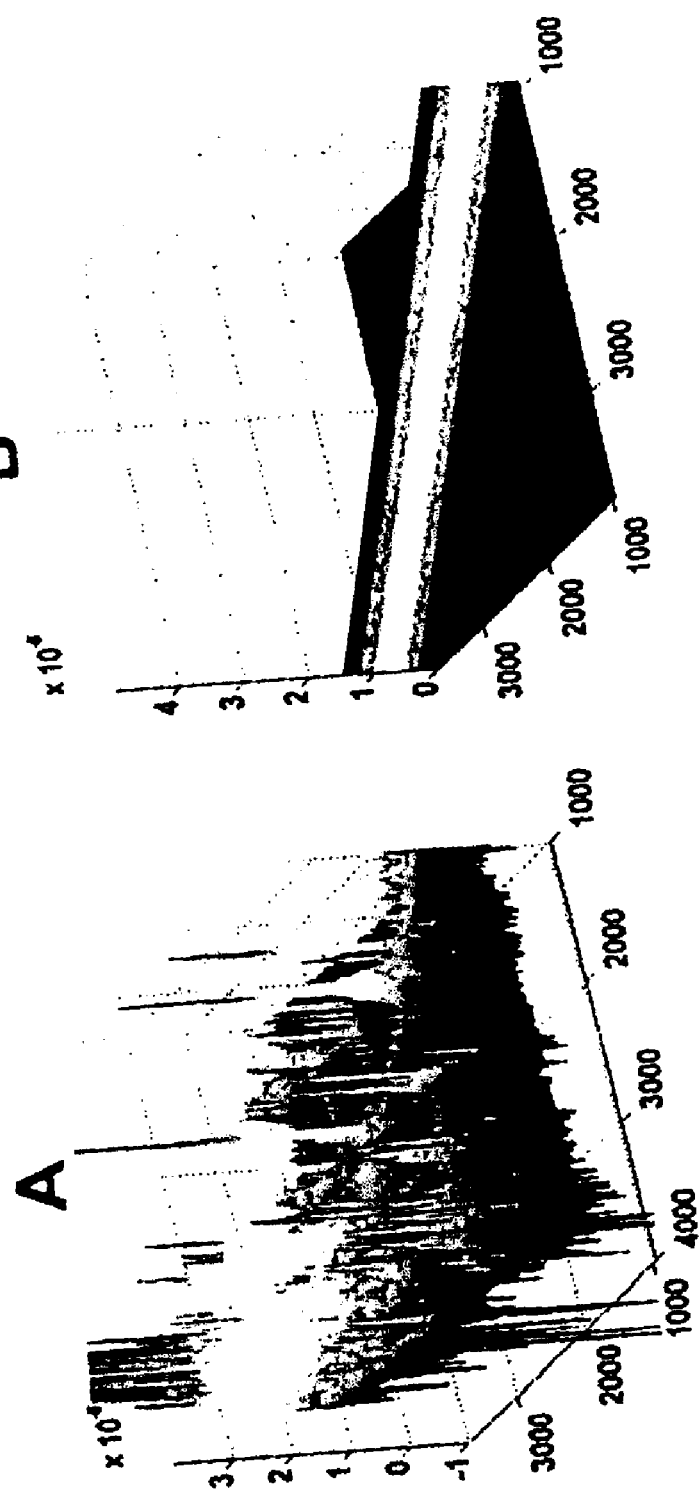
FIG. 16A shows the covariance error structure of the mean-centered repeat spectra.
FIG. 16B shows the ideal error covariance structure assumed for standard least-squares analyses.

The non-uniform and correlated nature of the noise in the spectral images can best be observed by forming the error covariance matrix from the mean-centered repeat image spectral differences. This two-dimensional representation of the spectral error in the image is shown in FIG. 16A. FIG. 16B shows the ideal noise behavior of uniform variance and uncorrelated errors (i.e., only diagonal elements of constant magnitude). Clearly, the true error covariance structure of the spectral image data has non-uniform diagonal variance components and large off-diagonal terms, demonstrating that errors are highly correlated between frequencies. Thus, the errors observed from the measured spectral image data are a far departure from the ideal behavior presented in FIG. 16B.

The non-constant noise variance for infrared absorbance spectra is expected, since the log transformation required to obtain absorbance spectra takes noise variance that is expected to be constant at all frequencies for MCT detectors and makes the noise nonuniform over the spectral frequencies. The expected form of the noise variance of the difference of two repeat absorbance spectra at a single frequency can be estimated as outlined below.

$$A = \log\frac{(I_s + \sigma_{s1})}{(I_s + \sigma_{s2})} = \log(I_s + \sigma_{s1}) - \log(I_s + \sigma_{s2}) \quad (25)$$

where $I_s$ is the noise-free single-beam intensity of the two repeat sample spectra and $\sigma_{s1}$ and $\sigma_{s2}$ are the standard deviations of the noise from repeat spectra 1 and 2, respectively. From Eq. (25), estimates of the error variances in absorbance $(\sigma_A^2)$ can be obtained by taking a Taylor series expansion of the error variance in the single-beam intensities in Eq. (25) and retaining only the first non-zero term for both terms on the right-hand side of Eq. (25). The result is:

$$\sigma_A^2 \approx \left(\frac{\delta A}{\delta I_s}\right)\sigma_{s1}^2 + \left(\frac{\delta A}{\delta I_s}\right)\sigma_{s2}^2 = \frac{\sigma_{s1}^2}{I_s^2} + \frac{\sigma_{s2}^2}{I_s^2} \approx \frac{2\sigma_s^2}{I_s^2} \quad (26)$$

where the last term on the right-hand side of Eq. (26) assumes that the error variance is comparable for both repeat single-beam spectra. From Eq. (26), the error variance for the absorbance spectra is inversely proportional to the square of the single-beam intensity for the infrared spectrum. In a simple weighted least squares fit of the data, the weights would be proportional to the square root of the inverse of the spectral absorbance variance. If experimental estimates follow the expected theory, then the approximate proper weights would be proportional to the average single beam spectrum obtained from the image spectra.

Figure 17:
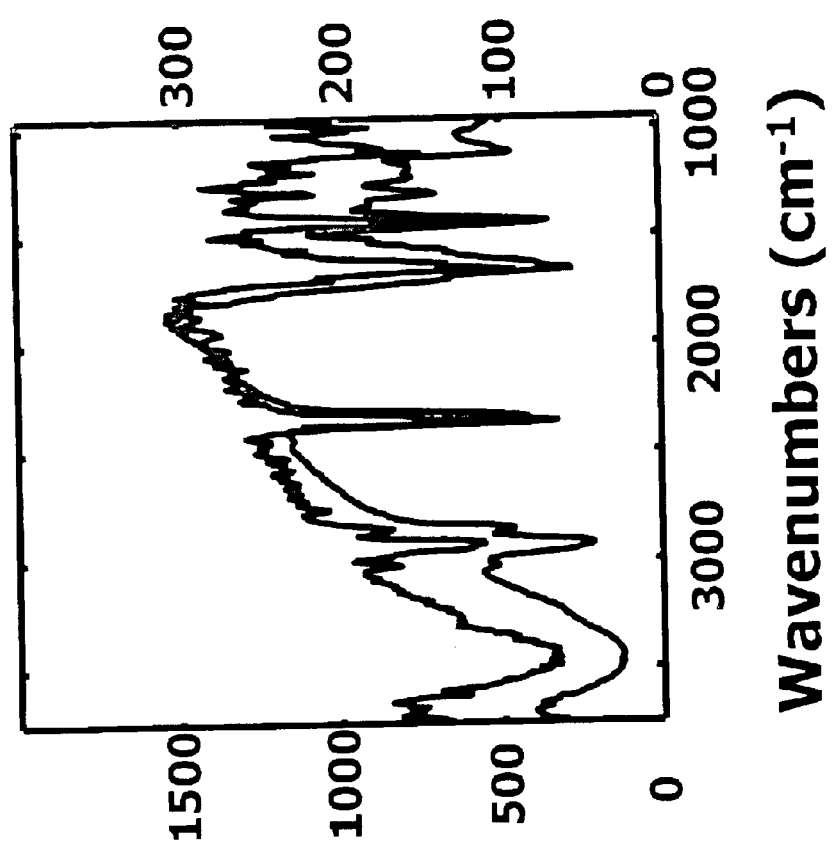
FIG. 17 depicts the experimental and theoretical estimates for the weighting function. The upper trace is the inverse of the square root of the variance component from the mean-centered repeat spectra (left axis). The lower trace is the average single-beam spectrum of the neoprene pixels (right axis).

FIG. 17 compares the estimated weighting function for absorbance error variance obtained from the repeat sample image differences and the theoretical weighting function based on the average single-beam intensity obtained from the sample image data. Clearly, the experimental and theoretical estimates for the weighting function are very similar, demonstrating that the repeat spectral differences can lead to reasonable estimates for the error variance of the absorbance spectral data. Confirmation that the full covariance structure of the residual is captured by the repeat image spectral differences enables the use of this information to reduce or eliminate systematic errors during the image analysis.

Figure 13B:
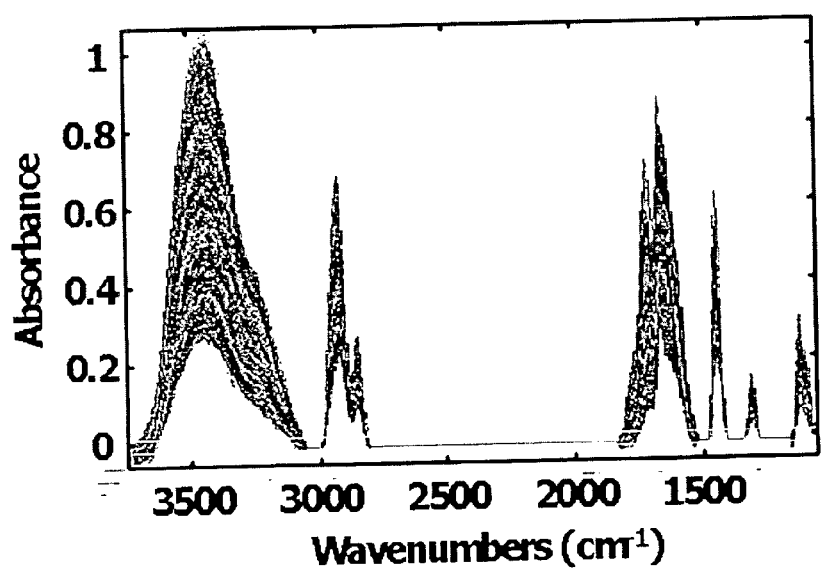
FIG. 13B depicts spectra of neoprene bands from spectral image of the sample after removing a linear baseline from each of the 6 neoprene related spectral bands.
Figure 14A:
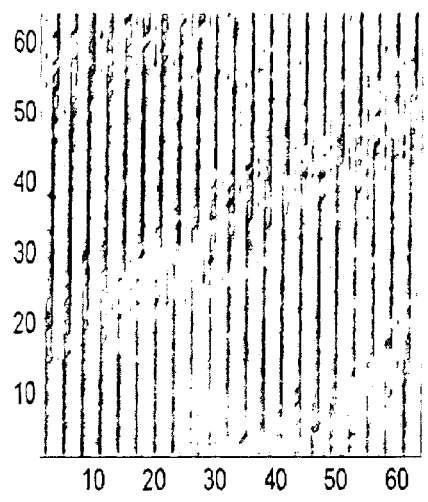
FIG. 14A shows scores from factor 5 of an interferogram.
Figure 14B:
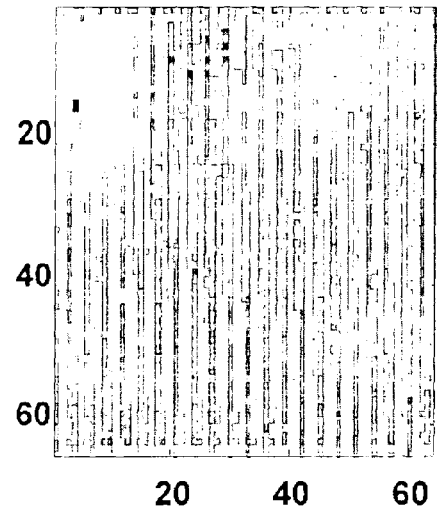
FIG. 14B shows scores from factor 10 of the negative log of a sample single beam.
Figure 14C:
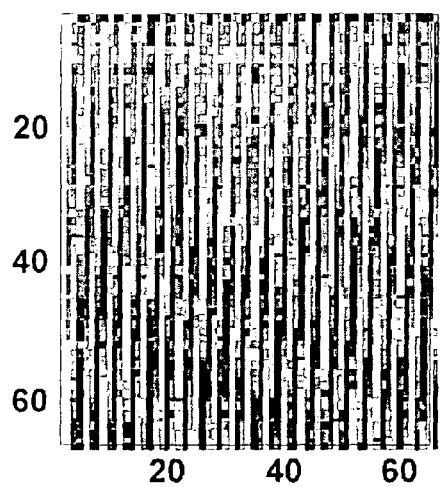
FIG. 14C shows scores from factor 2 of two ratioed background single-beam spectra after conversion to absorbance.
Figure 14D:
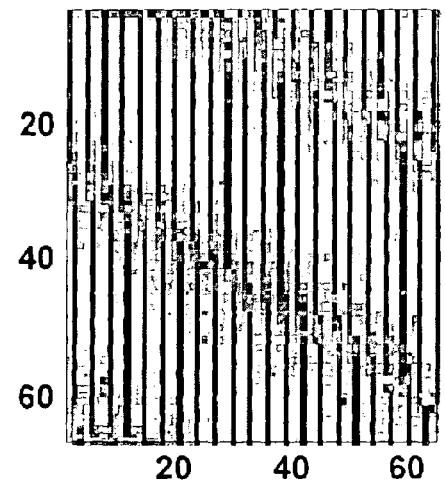
FIG. 14D shows scores from factor 3 from same two ratioed background single-beam spectra after conversion to absorbance.
Figure 18:
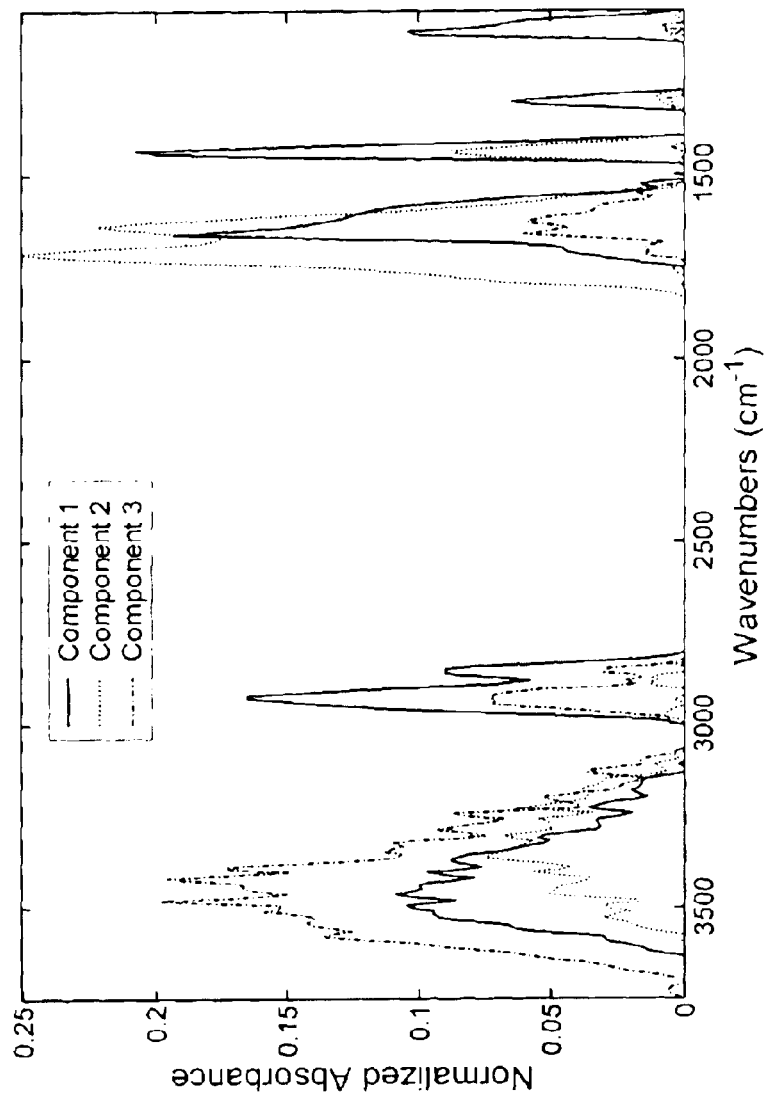
FIG. 18 depicts the estimated pure-component spectra using standard non-negativity constrained MCR.

Conventional MCR methods were applied to the spectral image data presented in FIG. 13B using non-negativity constraints on both concentrations and pure-component spectra. Three pure components appeared to be adequate to represent the original thermally modified neoprene and the decomposition products. Using more than three pure components yielded results that were not as physically meaningful as obtained with three components only. The normalized MCR pure-component spectra obtained with three components are presented in FIG. 18. The trace corresponding to component 1 is characteristic of the thermally aged but unoxidized neoprene sample. The component 2 trace indicates a decomposition product that contains a significant carbonyl decomposition product. The component 3 trace indicates that a second decomposition product is present in the aged sample that is characterized by a hydroxyl dominated decomposition product with very little formation of a carbonyl species. This second decomposition product has a different spatial profile in the sample than the first. The high-frequency region of the pure-component spectra is quite noisy.

Figure 19:
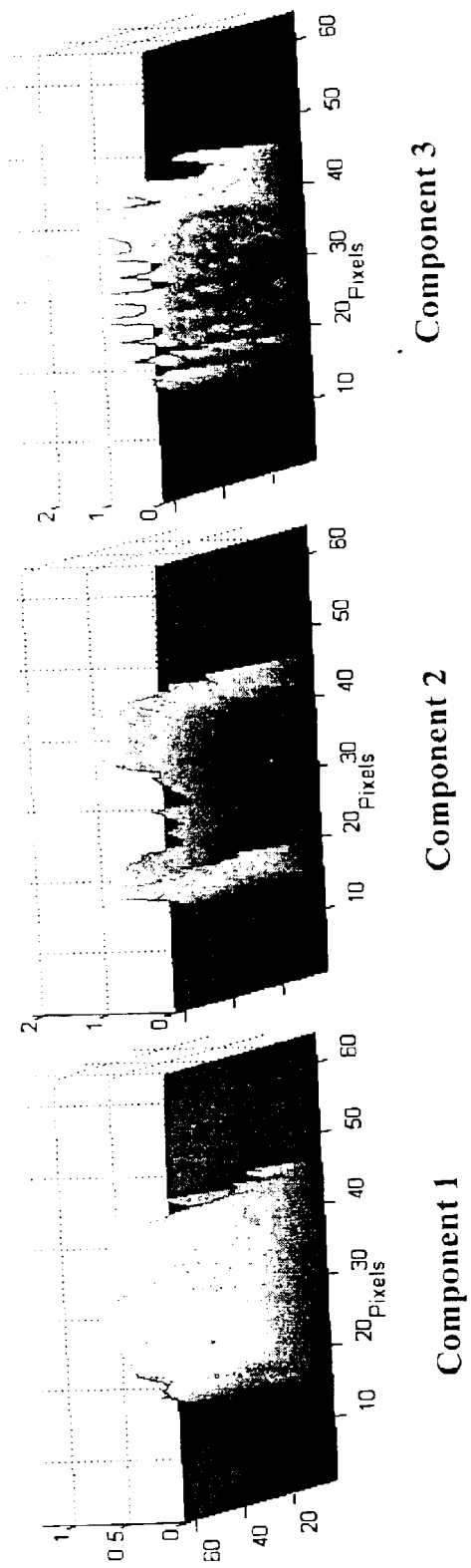
FIG. 19 depicts the concentration maps for components 1, 2, and 3 obtained from the standard non-negativity constrained MCR.

Pathlength-corrected relative concentration maps representing the three pure components are presented in FIG. 19. Some of the striped artifact presented in FIG. 14 is clearly visible in at least two of these concentration maps, indicating that the MCR analyses are corrupted by this artifact. The carbonyl decomposition product (component 2 in FIG. 19) demonstrates a large concentration gradient that is high at the outer edges of the sample. The hydroxyl component decomposition product shown as component 3 in FIG. 19 is more variable and extends somewhat beyond the region containing the carbonyl decomposition product. The thermally aged but unoxidized neoprene shown as component 1 in FIG. 19 is present somewhat uniformly throughout the sample although it may have been reduced near the edge of the sample by the oxidation.

Figure 20:
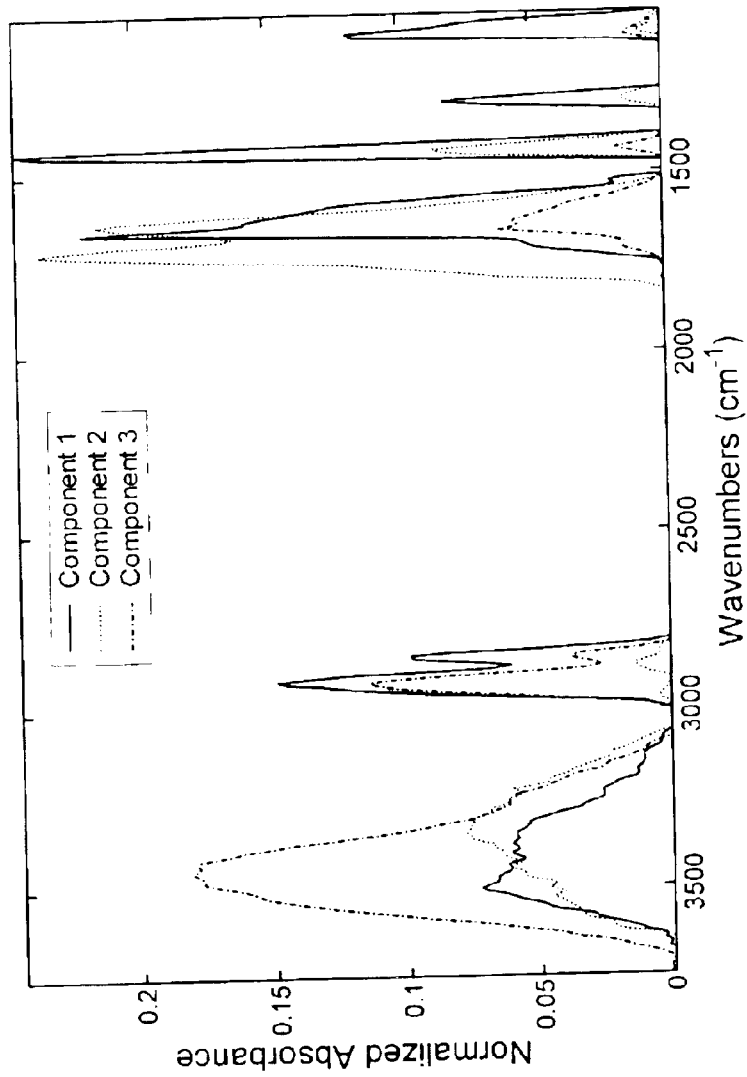
FIG. 20 depicts the estimated pure-component spectra obtained by augmenting with the first five scores from the mean-centered repeat spectra and using non-negativity and equality constrained MCR.

MCR was then applied to the same spectral image data with the concentration matrix augmented by the first five sets of scores from the mean-centered repeat image spectral differences, according to the ACLS method of the present invention. The score-augmented MCR was implemented with equality constraints on these five sets of image scores. In applying these equality constraints on the scores, the alternating classical least-squares generation of the pure-component spectra is corrected for the presence of score-related concentration errors in the image data. FIG. 20 presents the three pure-component spectra generated from the MCR augmented with the scores. Note that the noise in the high-energy region of the pure-component spectra is greatly reduced in these pure-component estimates as compared to FIG. 18. In addition, more detailed structure becomes available in the OH stretching region of the spectra (3000–3700 cm$^{-1}$ spectral region) with score augmentation. The derivative nature of the hydroxyl band for the carbonyl dominated decomposition product (component 2) may indicate some hydrogen bonding with the hydroxyl dominated decomposition product. Since the concentrations were not corrected when augmenting with scores only, the concentration maps indicate essentially no improvement in the striping artifact relative to the standard non-augmented MCR analysis of the same data.

Figure 21:
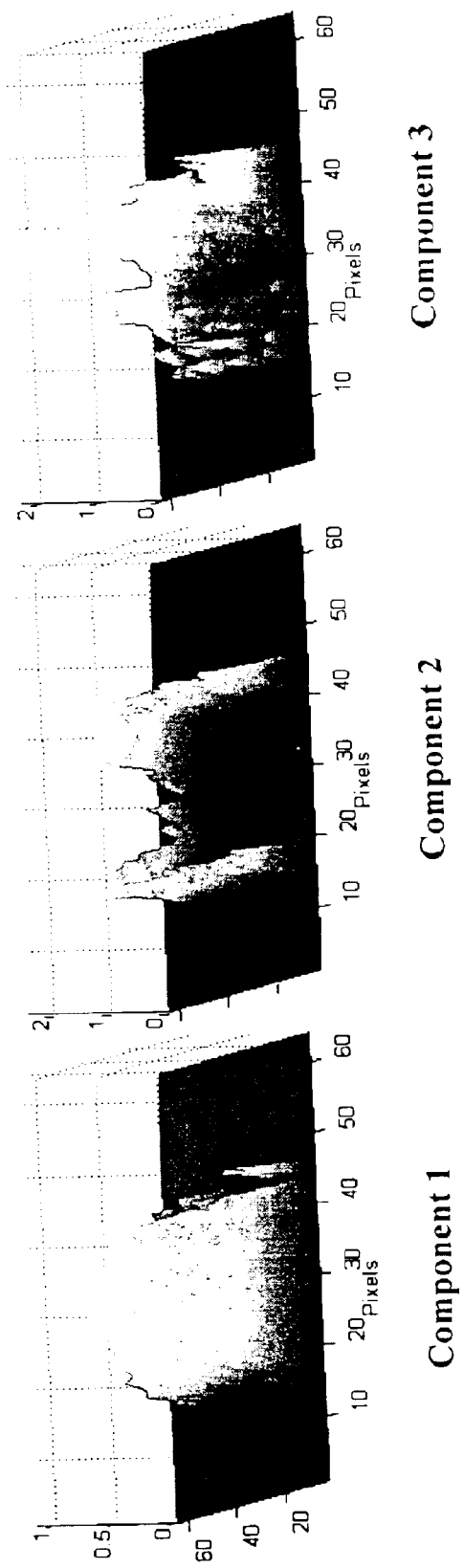
FIG. 21 depicts the concentration maps for components 1, 2, and 3 obtained by augmenting with the first five eigenvectors from the mean-centered repeat spectra and using non-negativity and equality constrained MCR.

MCR was then applied to the same spectral image data with the first five sets of eigenvectors from the mean-centered repeat image spectral differences added to the pure-component spectral matrix. The eigenvector-augmented MCR was implemented with equality constraints on these five eigenvectors. With eigenvector augmentation only, there was some improvement in noise of the high-energy side of the hydroxyl-dominated pure component, but there was little, if any, improvement in the noise on the other pure-component spectra. However, the concentration maps exhibit dramatic improvement in the quality. The striping artifact was nearly completely removed when the eigenvectors augment the MCR, as shown in FIG. 21. These improvements in concentration maps were expected since the augmentation of the pure-component spectra with the eigenvectors corrects the concentration estimates.

Figure 22:
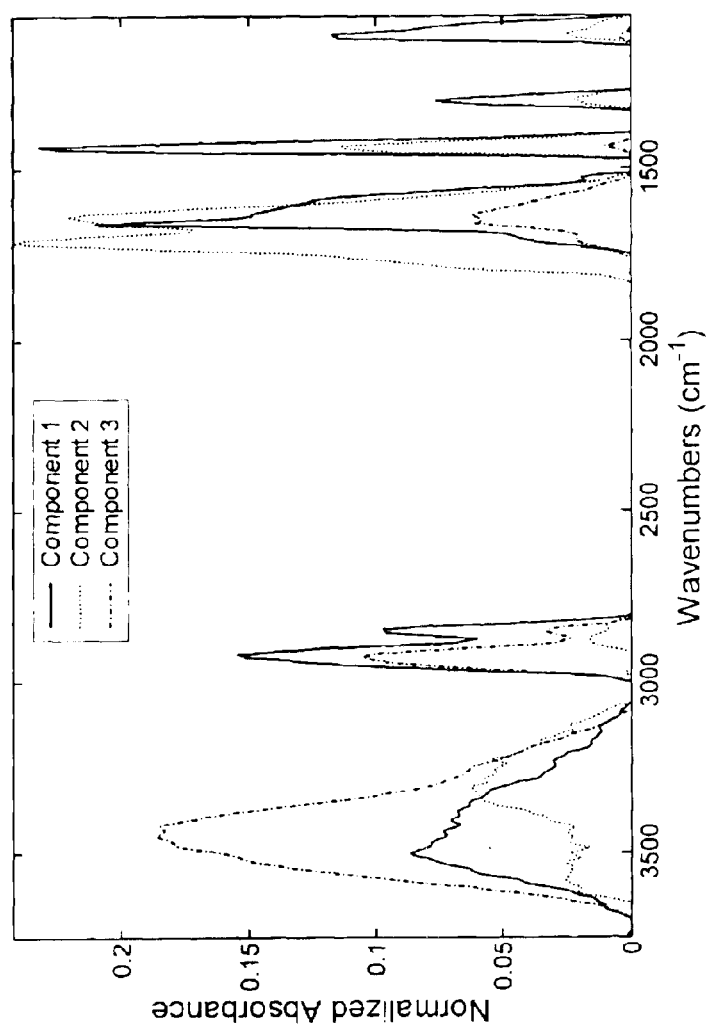
FIG. 22 depicts the estimated pure-component spectra obtained by augmenting with the first five sets of scores and eigenvectors from the mean-centered repeat spectra and using non-negativity and equality constrained MCR.
Figure 23:
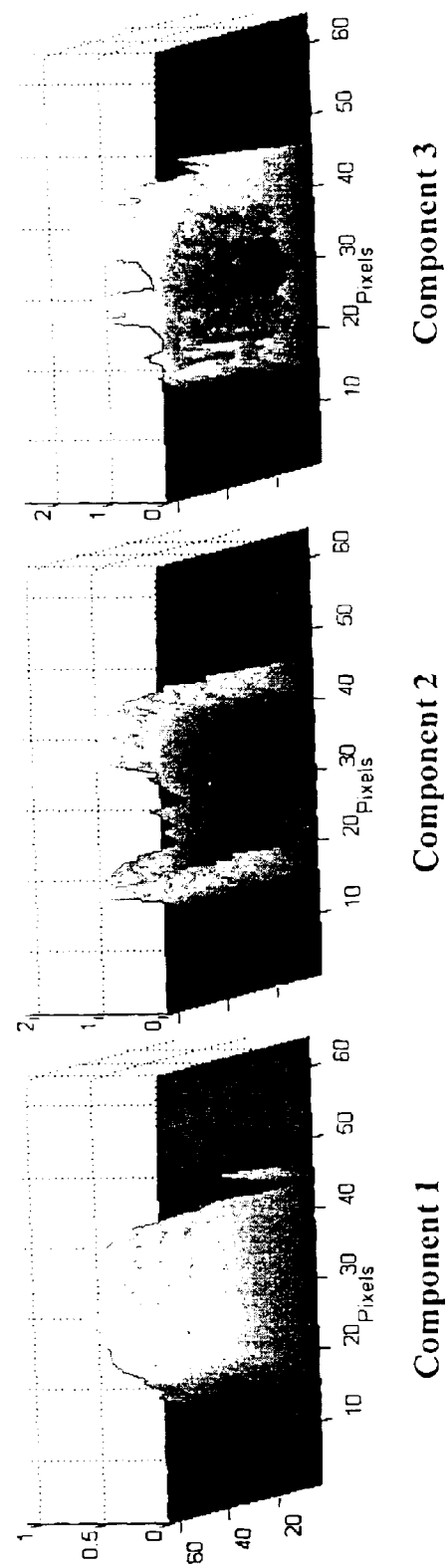
FIG. 23 depicts the concentration maps for components 1, 2, and 3 obtained by augmenting with the first five sets of scores and eigenvectors from the mean-centered repeat spectra and using non-negativity and equality constrained MCR.
Figure 24:
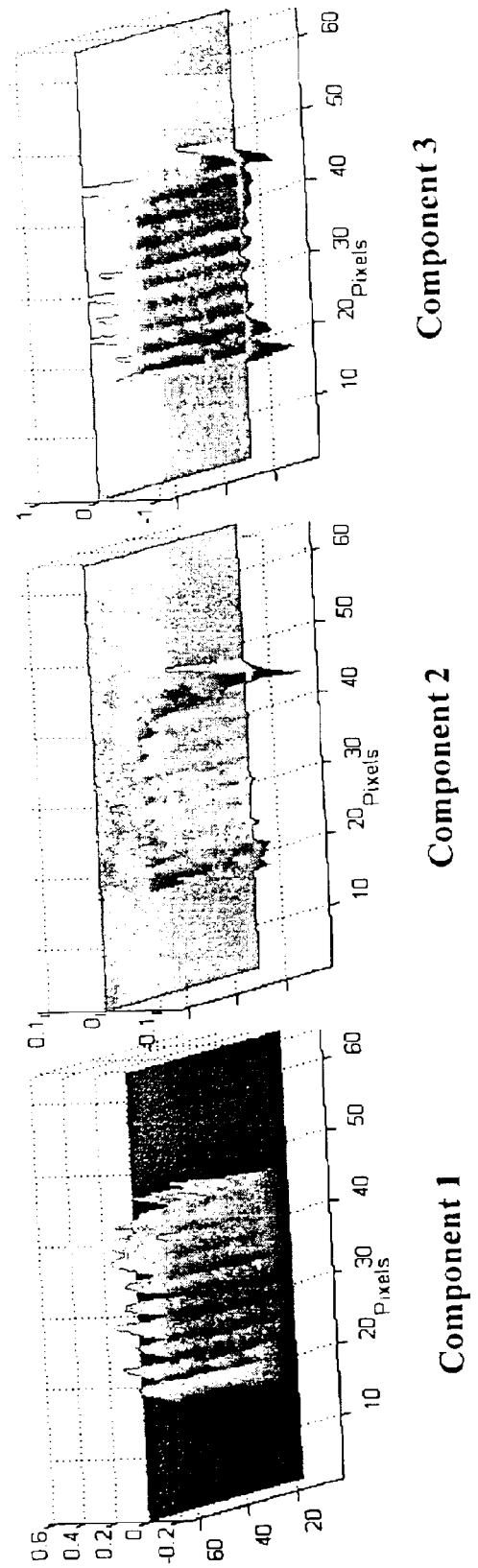
FIG. 24 depicts the differences in the concentration maps of components 1, 2, and 3 from the standard MCR and MCR augmented with the first five sets of scores and eigenvectors from the mean-centered repeat image spectra of the neoprene pixels.

Finally, the MCR analysis was augmented with both scores and eigenvectors from the repeat image spectral differences. In this embodiment of the present invention, one simply augments with scores during the calibration phase of the MCR and augments with the eigenvectors during the prediction phase. Thus, at each iteration in the MCR procedure, any estimates related to the augmented vectors are replaced with the original eigenvectors from the PCA decomposition of the repeat image differences. The combined augmentation with scores and eigenvectors generates both improved pure-component spectra and corrected concentration maps. The pure-component spectra with scores and eigenvector augmentation are presented in FIG. 22. These spectra have the low noise of the scores-augmented MCR and are also slightly modified, especially in the high-energy hydroxyl spectral region. The concentration maps with scores- and eigenvector-augmented MCR are presented in FIG. 23. Like the eigenvector-augmented MCR concentration maps, these images exhibit greatly reduced striping artifact. The reduction in the artifact is emphasized in FIG. 24, which shows the difference between the standard MCR and the fully augmented MCR concentration maps for all three components (i.e., the difference between the concentration maps in FIG. 23 and FIG. 19). As indicated by this difference map, a significant reduction in the system artifact was achieved when augmenting with estimates of the error covariance information derived from the difference between two repeat images.

Having thus described the present invention with particularity and demonstrated its utility with respect to both simulated and actual experimental data, those skilled in the art will appreciate that the present invention has broad applicability to a wide range of opportunities for analyzing multivariate spectral data and obtaining both qualitative and quantitative results. Many preprocessing procedures such as centering, scaling, path-length correction, smoothing, derivatives, multiplicative signal correction, PCA, wavelet compression, and covariance filtering have been developed that can be performed on the measured spectra when using the present invention.

What is claimed is:

1. A method of multivariate spectral analysis, comprising the steps of:

a) obtaining an estimate of spectral error covariance $E_A$ for measured set of multivariate spectral data A;

b) decomposing the spectral error covariance $E_A$ according to $E_A = TP + E$, where T is a set of n×r scores and P is a set of r×p loading vectors obtained from factor analysis of the spectral error covariance $E_A$, and E is a set of n×p random errors and spectral variations not useful for prediction;

c) guessing pure-component spectra K for the set of multivariate spectral data A;

d) predicting a set of component values $\hat{C}$ according to $$\hat{C} A K^T (K K^T)^{-1} = A (K^T)^+;$$

e) augmenting the set of predicted component values $\hat{C}$ with at least one vector of the T scores to obtain a first set of augmented component values $$\hat{\tilde{C}};$$

f) estimating augmented pure-component spectra $$\hat{\tilde{K}}$$

according to $$\hat{\tilde{K}} = (\tilde{C}^T \tilde{C})^{-1} \tilde{C}^T A = \hat{\tilde{C}}^+ A;$$

g) testing for convergence according to $$\left\| A - \hat{\tilde{C}} \hat{\tilde{K}} \right\|^2;$$

h) predicting a second set of augmented component values $$\hat{\tilde{C}}$$

according to $$\hat{\tilde{C}} = A\hat{\tilde{K}}^T\left(\hat{\tilde{K}}\hat{\tilde{K}}^T\right)^{-1} = A(\hat{\tilde{K}}^T)^+;$$

i) replacing the augmented portion of the second set of augmented component values $$\hat{\tilde{C}}$$

with the at least one vector of the T scores to obtain a third set of augmented component values $$\hat{\tilde{C}};$$

and j) repeating steps f) through i) at least once.

2. The method of claim 1, wherein the steps f) through i) are repeated until the test of step g) converges to obtain an alternating classical least squares solution for $$\hat{\tilde{K}}$$

and $$\hat{\tilde{C}}.$$

3. The method of claim 1, further comprising replacing the augmented portion of the augmented pure-component spectra $$\hat{\tilde{K}}$$

with at least one vector of the P loading vectors prior to step h).

4. The method of claim 1, further comprising augmenting $$\hat{\tilde{K}}$$

with at least one vector representing a spectral shape that is representative of at least one additional source of spectral variation prior to step h).

5. The method of claim 1, further comprising applying at least one constraint to the non-augmented portion of $$\hat{\tilde{K}}$$

at step f).

6. The method of claim 5, wherein the at least one constraint is selected from the group consisting of non-negativity, equality, closure, monotonic constraint, unimodality, and selectivity.

7. The method of claim 1, further comprising applying at least one constraint to the non-augmented portion of $$\hat{\tilde{C}}$$

at step h).

8. The method of claim 7, wherein the at least one constraint is selected from the group consisting of non-negativity, equality, closure, monotonic constraint, unimodality, and selectivity.

9. The method of claim 1, wherein the guessed pure-component spectra K comprises random numbers.

10. The method of claim wherein the measured set of multivariate spectral data A comprises image data.

11. The method of claim 10, wherein the spectral error covariance $E^A$ is obtained from a shift difference generated from a single image.

12. The method of claim 10, wherein the spectral error covariance $E^A$ is obtained from repeat image spectra.

13. A method of multivariate spectral analysis, comprising the steps of:

a) obtaining an estimate of spectral error covariance $E_A$ for measured set of multivariate spectral data A;

b) decomposing the spectral error covariance $E_A$ according to $E_A = TP+E$, where T is a set of n×r scores and P is a set of r×p loading vectors obtained from factor analysis of the spectral error covariance $E_A$, and E is a set of n×p random errors and spectral variations not useful for prediction;

c) guessing pure-component spectra K for the set of multivariate spectral data A;

d) augmenting the pure-component spectra K with at least one vector of the P loading vectors to obtain first augmented pure-component spectra $\tilde{K}$;

e) predicting a first set of augmented component values $$\hat{\tilde{C}}$$

according to $$\hat{\tilde{C}} = A\tilde{K}^T\left(\tilde{K}\tilde{K}^T\right)^{-1} + A(\tilde{K}^T)^+;$$

f) estimating second augmented pure-component spectra $$\hat{\tilde{K}}$$

according to $$\hat{\tilde{K}} = \left(\hat{\tilde{C}}^T\hat{\tilde{C}}\right)^{-1}\hat{\tilde{C}}^T A = \hat{\tilde{C}}^+ A;$$

g) testing for convergence according to $$\left\|A - \hat{\tilde{C}}\hat{\tilde{K}}\right\|^2;$$

h) replacing the augmented portion of the second augmented pure-component spectra $$\hat{\tilde{K}}$$

with the at least one vector of the P loading vectors to obtain third augmented pure-component spectra $\hat{\hat{K}}$;

and i) predicting a second set of augmented component values $\hat{\hat{C}}$ according to $$\hat{\hat{C}} = A\hat{\hat{K}}^T\left(\hat{\hat{K}}\hat{\hat{K}}^T\right)^{-1} = A(\hat{\hat{K}}^T)^+;$$

j) repeating steps f) through i) at least once.

14. The method of claim 13, wherein the steps f) through i) are repeated until the test of step g) converges to obtain an alternating classical least squares solution for $\hat{\hat{K}}$ and $\hat{\hat{C}}$.

15. The method of claim 14, wherein the measured set of multivariate spectral data A comprises image data.

16. The method of claim 13, further comprising replacing the augmented portion of the set of augmented component values $\hat{\hat{C}}$ with at least one vector of the T scores prior to step h).

17. The method of claim 13, further comprising augmenting $\hat{\hat{K}}$ with at least one vector representing a spectral shape that is representative of at least one additional source of spectral variation prior to step h).

18. The method of claim 13, further comprising applying at least one constraint to the non-augmented portion of $\hat{\hat{K}}$ at step f).

19. The method of claim 18, wherein the at least one constraint is selected from the group consisting of non-negativity, equality, closure, monotonic constraint, unimodality, and selectivity.

20. The method of claim 13, further comprising applying at least one constraint to the non-augmented portion of $\hat{\hat{C}}$ at step h).

21. The method of claim 20, wherein the at least one constraint is selected from the group consisting of non-negativity, equality, closure, monotonic constraint unimodality, and selectivity.

22. The method of claim 13, wherein the guessed pure-component spectra K comprises random numbers.

23. The method of claim 13, wherein the measured set of multivariate spectral data A comprises image data.

24. The method of claim 23, wherein the estimate of the error covariance $E_A$ is obtained from a shift difference generated from a single image.

25. The method of claim 23, wherein the estimate of the error covariance $E_A$ is obtained from repeat image spectra.

26. The method of claim 25, wherein the spectral error covariance $E_A$ is obtained from a shift difference generated from a single image.

27. The method of claim 25, wherein the spectral error covariance $E_A$ is obtained from repeat image spectra.

28. A method of multivariate spectral analysis, comprising the steps of:
  a) obtaining an estimate of the spectral error covariance $E_A$ for measured set of multivariate spectral data A;
  b) decomposing the spectral error covariance $E_A$ according to $E_A$=TP+E, where T is a set of n×r scores and P is a set of r×p loading vectors obtained from factor analysis of the spectral error covariance $E_A$, and E is a set of n×p random errors and spectral variations not useful for prediction;
  c) guessing a set of component values C for the set of multivariate spectral data A;
  d) estimating pure-component spectra $\hat{K}$ according to $\hat{K}=(C^TC)^{-1}C^TA=C^+A$;
  e) augmenting the pure-component spectra $\hat{K}$ with at least one vector of the P loading vectors to obtain first augmented pure-component spectra $\hat{\hat{K}}$;

f) predicting a first set of augmented component values $\hat{\hat{C}}$ according to $$\hat{\hat{C}} = A\hat{\hat{K}}^T\left(\hat{\hat{K}}\hat{\hat{K}}^T\right)^{-1} = A(\hat{\hat{K}}^T);$$

g) testing for convergence according to $$\left\|A - \hat{\hat{C}}\hat{\hat{K}}\right\|^2;$$

h) estimating second augmented pure-component spectra $\hat{\hat{K}}$ according to $$\hat{\hat{K}} = \left(\hat{\hat{C}}^T\hat{\hat{C}}\right)^{-1}\hat{\hat{C}}^T A = \hat{\hat{C}}^+ A;$$

i) replacing the augmented portion of the second augmented pure-component spectra $\hat{\tilde{K}}$ with the at least one vector of the P loading vectors to obtain a third augmented pure-component spectra $\hat{\tilde{K}}$ and j) repeating steps f) through i) at least once.

29. The method of claim 28, wherein the steps f) through i) are repeated until the test of step g) converges to obtain an alternating classical least squares solution for $\hat{\tilde{K}}$ and $\hat{\tilde{C}}$.

30. The method of claim 28, further comprising replacing the augmented portion of the set of augmented component values $\hat{\tilde{C}}$ with at least one vector of the T scores prior to step h).

31. The method of claim 28, further comprising augmenting $\hat{\tilde{K}}$ with at least one vector representing a spectral shape that is representative of at least one additional source of spectral variation prior to step h).

32. The method of claim 28, further comprising applying at least one constraint to the non-augmented portion of $\hat{\tilde{K}}$ at step h).

33. The method of claim 32, wherein the at least one constraint is selected from the group consisting of non-negativity, equality, closure, monotonic constraint, unimodality, and selectivity.

34. The method of claim 28, further comprising applying at least one constraint to the non-augmented portion of $\hat{\tilde{C}}$ at step f).

35. The method of claim 34, wherein the at least one constraint is selected from the group consisting of non-negativity, equality, closure, monotonic constraint unimodality, and selectivity.

36. The method of claim 28, wherein the guessed set of component values C comprises random numbers.

37. A method of multivariate spectral analysis, comprising the steps of:

a) obtaining an estimate of the spectral error covariance $E_A$ for measured set of multivariate spectral data A;

b) decomposing the spectral error covariance $E_A$ according to $E_A = TP + E$, where T is a set of n×r scores and P is a set of r×p loading vectors obtained from factor analysis of the spectral error covariance $E_A$, and E is a set of n×p random errors and spectral variations not useful for prediction;

c) guessing a set of component values C for the set of multivariate spectral data A;

d) augmenting the set of component values C with at least one vector of the T scores to obtain a first set of augmented component values $\tilde{C}$;

e) estimating augmented pure-component spectra $\hat{\tilde{K}}$ according to $$\hat{\tilde{K}} = (\tilde{C}^T \tilde{C})^{-1} \tilde{C}^T A = \tilde{C}^+ A;$$

f) testing for convergence according to $$\left\| A - \tilde{C}\hat{\tilde{K}} \right\|^2;$$

g) predicting a second set of augmented component values $\hat{\tilde{C}}$ according to $$\hat{\tilde{C}} = A\tilde{K}^T \left( \hat{\tilde{K}} \hat{\tilde{K}}^T \right)^{-1} A(\hat{\tilde{K}}^T)^+;$$

h) replacing the augmented portion of the second set of augmented component values $\hat{\tilde{C}}$ with the at least one vector of the T scores to obtain a third set of augmented component values $\hat{\tilde{C}}$ and i) repeating steps e) through h) at least once, using the augmented component values $\hat{\tilde{C}}$ in step f).

38. The method of claim 37, wherein the steps e) through h) are repeated until the test of step g) converges to obtain an alternating classical least squares solution for $$\hat{\tilde{K}}$$

and $$\hat{\tilde{C}}$$

39. The method of claim 37, further comprising replacing the augmented portion of the augmented pure-component spectra $$\hat{\tilde{K}}$$

with at least one vector of the P loading vectors prior to step e).

40. The method of claim 37, further comprising augmenting $$\hat{\tilde{K}}$$

with at least one vector representing a spectral shape that is representative of at least one additional source of spectral variation prior to step e).

41. The method of claim 37, further comprising applying at least one constraint to the non-augmented portion of $$\hat{\tilde{K}}$$

at step e).

42. The method of claim 41, wherein the at least one constraint is selected from the group consisting of non-negativity, equality, closure, monotonic constraint, unimodality, and selectivity.

43. The method of claim 37, further comprising applying at least one constraint to the non-augmented portion of $$\hat{\tilde{C}}$$

at step g).

44. The method of claim 43, wherein the at least one constraint is selected from the group consisting of non-negativity, equality, closure, monotonic constraint unimodality, and selectivity.

45. The method of claim 37, wherein the guessed set of component values C comprises random numbers.

46. The method of claim 37, wherein the measured set of multivariate spectral data A comprises image data.

47. The method of claim 46, wherein the spectral error covariance $E_A$ is obtained from a shift difference generated from a single image.

48. The method of claim 46, wherein the spectral error covariance $E_A$ is obtained from repeat image spectra.

* * * * *